(12) United States Patent
Kim et al.

(10) Patent No.: US 7,595,323 B2
(45) Date of Patent: Sep. 29, 2009

(54) N-PHENYL-2-PYRIMIDINE-AMINE DERIVATIVES AND PROCESS FOR THE PREPARATION THEREOF

(75) Inventors: Dong-Yeon Kim, Songpa-gu (KR); Jae-Gun Kim, Suwon (KR); Dae-Jin Cho, Suwon (KR); Gong-Yeal Lee, Yongin (KR); Hong-Youb Kim, Suwon (KR); Seok-Hun Woo, Suwon (KR); Yong-Seok Kim, Sungnam (KR); Woo-Chul Bae, Suwon (KR); Sun-Ahe Lee, Suwon (KR); Byoung-Cheol Han, Dangjin-geun (KR)

(73) Assignee: IL Yang Pharm. Co., Ltd., Yongin (KR)

( * ) Notice: Subject to any disclaimer, the term of this patent is extended or adjusted under 35 U.S.C. 154(b) by 38 days.

(21) Appl. No.: 10/806,834

(22) Filed: Mar. 22, 2004

(65) Prior Publication Data

US 2004/0248918 A1    Dec. 9, 2004

Related U.S. Application Data

(63) Continuation-in-part of application No. 10/446,446, filed on May 28, 2003, now abandoned.

(30) Foreign Application Priority Data

May 6, 2003    (KR) ..................... 10-2003-0028669

(51) Int. Cl.
*C07D 239/28* (2006.01)
*A61K 31/505* (2006.01)

(52) U.S. Cl. .................. 514/255.05; 514/275; 544/275; 544/295; 544/331

(58) Field of Classification Search ............... 424/94.63
See application file for complete search history.

(56) References Cited

U.S. PATENT DOCUMENTS 7,081,532 B2 * 7/2006 Buerger et al. .............. 544/295
2004/0028673 A1 * 2/2004 Netzer et al. ............. 424/94.63

FOREIGN PATENT DOCUMENTS

| KR | 1993-0021624 | | 11/1993 |
| KR | 2001-0021950 | | 3/2001 |
| WO | WO 99/03854 | | 1/1999 |
| WO | WO-9903854 | * | 1/1999 |

* cited by examiner

*Primary Examiner*—Alton N Pryor
(74) *Attorney, Agent, or Firm*—Edwards Angell Palmer & Dodge LLP; Peter F. Corless; Nicholas J. DiCeglie, Jr.

(57) ABSTRACT

The present invention relates to an N-phenyl-2-pyrimidine-amine derivative showing a superior effect on lung cancer, gastric cancer, colon cancer, pancreatic cancer, hepatoma, prostatic cancer, breast cancer, chronic or acute leukemia, hematologic malignancy, encephalophyma, bladder cancer, rectal cancer, or cervical cancer, etc. of warm-blooded animals and its salt. The present invention also relates to a process for preparing the compound, and to a pharmaceutical composition for the treatment of the above various diseases, which comprises an effective amount of the compound as an active ingredient together with pharmaceutically acceptable inert carriers.

7 Claims, 1 Drawing Sheet

N-PHENYL-2-PYRIMIDINE-AMINE DERIVATIVES AND PROCESS FOR THE PREPARATION THEREOF

This application is a continuation-in-part of Ser. No. 10/446,446 filed on May 28, 2003 now abandoned as N-Phenyl-2-Pyrimidine-Amine Derivatives and Process for the Preparation Thereof.

TECHNICAL FIELD

The present invention relates to a N-phenyl-2-pyrimidine-amine derivative represented by the following formula (1), which shows a superior therapeutic effect on lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, etc. of warm-blooded animals:

(1)

and its salt, in which $R_1$ represents 3-pyridyl or 4-pyridyl, $R_2$ and $R_3$ each represent hydrogen or lower alkyl, $R_6$ or $R_7$ represents a radical having the following formula (2):

(2)

wherein X represents oxygen or NH, n=0 or 1, and $R_9$ represents aliphatic having 5 to 10 carbon atoms, or represents 5 to 7 membered saturated or unsaturated monocyclic radical, or bi- or tri-cyclic radical optionally combined with a benzene ring(s), each of which has 1 to 3 hetero atoms selected from a group consisting of nitrogen, oxygen and sulfur, or represents piperazinyl or homopiperazinyl each of which is substituted by lower alkyl, and $R_4$, $R_5$, $R_7$, and $R_8$ each represent hydrogen, or one or two thereof each represent halogen, lower alkyl, or lower alkoxy when $R_6$ represents the radical of the above formula (2), or one or two of $R_4$, $R_5$, $R_6$, and $R_8$ each represent halogen, lower alkyl, or lower alkoxy when $R_7$ represents the radical of the above formula (2), provided that $R_6$ or $R_7$ represents a radical of formula (2) wherein n=0 and $R_9$ is 4-methylpiperazine, then one or more of $R_4$, $R_5$, $R_7$, and $R_8$, or one or more of $R_4$, $R_5$, $R_6$, and $R_8$ are halogen.

The present invention also relates to a process for preparing the compound of formula (1) and a pharmaceutical composition for the treatment of such diseases as lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, etc., which comprises an effective amount of the compound of formula (1) or salt thereof as an active ingredient together with pharmaceutically acceptable inert carriers.

BACKGROUND ART

The earlier therapeutic agent for Chronic Myelogenous Leukemia (CML, below), Imatinib mesylate (Gleevec, Korean Patent Laid-open Publication No. 1993-0021624 and Korean Patent Laid-open Publication No. 2001-0021950), has the structure of the above formula (1) wherein the amide type radical of formula (2) (n=0) is substituted at the position of $R_7$, $R_4$ is methyl, and $R_9$ is methylpiperazine, and so shows restrictive therapeutic effect, low stability, and several problems in its manufacturing process. That is, since Imatinib mesylate has a high hygroscopic property, it may be easily deteriorated under the influence of the ambient moisture. Therefore, this compound should be recrystallized from a specific solvent such as methanol in order to maintain a specific crystal form, and should be used soon after its preparation. Further, this compound exhibits a therapeutic effect only on the CML and little effect on the other sites, differently from other anti cancer agents. It is synthesized in the order that 4-chloromethylbenzoic acid is combined first with N-methylpiperazine, chlorination is carried out using thionyl chloride, and the resulting side moiety is combined with the basic structure, wherein the use of thionyl chloride causes many problems such as generation of toxic gas, explosion, reduction of reaction yield, etc. Particularly, stability of the intermediate is not good to adversely affect the yield.

DISCLOSURE OF THE INVENTION

Thus, the present inventors have extensively and intensively studied to improve the problems as stated above. As a result, the inventors have identified that the novel compound of formula (1) as defined above exhibits a superior effect, and then completed the present invention.

Therefore, a purpose of the present invention is to provide a N-phenyl-2-pyrimidine-amine derivative of the following formula (1):

(1)

and its salt, in which $R_1$ represents 3-pyridyl or 4-pyridyl, $R_2$ and $R_3$ each represent hydrogen or lower alkyl, $R_6$ or $R_7$ represents a radical having the following formula (2):

(2)

wherein X represents oxygen or NH, n=0 or 1, and $R_9$ represents aliphatic having 5 to 10 carbon atoms, or represents 5 to 7 membered saturated or unsaturated monocyclic radical, or bi- or tri-cyclic radical optionally combined with a benzene ring(s), each of which has 1 to 3 hetero atoms selected from a group consisting of nitrogen, oxygen and sulfur, or represents piperazinyl or homopiperazinyl each of which is substituted by lower alkyl, and $R_4$, $R_5$, $R_7$, and $R_8$ each represent hydrogen, or one or two thereof each represent halogen, lower alkyl, or lower alkoxy when $R_6$ represents the radical of the above formula (2), or one or two of $R_4$, $R_5$, $R_6$, and $R_8$ each represent halogen, lower alkyl, or lower alkoxy when $R_7$ represents the radical of the above formula (2), provided that $R_6$ or $R_7$ represents a radical of formula (2) wherein n=0 and $R_9$ is 4-methylpiperazine, then one or more of $R_4$, $R_5$, $R_7$, and $R_8$, or one or more of $R_4$, $R_5$, $R_6$, and $R_8$ are halogen.

It is another purpose of the present invention to provide a process for preparing the compound of formula (1).

It is a further purpose of the present invention to provide a pharmaceutical composition for the treatment of such diseases as lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, etc., which comprises an effective amount of the compound of formula (1) or salt thereof as an active ingredient together with pharmaceutically acceptable inert carriers.

Below, the present invention will be explained in more detail.

BEST MODE FOR CARRYING OUT THE INVENTION

In the above definitions for the substituents of N-phenyl-2-pyrimidine-amine derivative of formula (1), which shows a superior effect to lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, etc. in warm-blooded animals, the term "lower alkyl" used alone or in a composite term with other terms preferably means straight-chain or branched and saturated aliphatic hydrocarbon radical having 1 to 6 carbon atoms such as methyl, ethyl, n-propyl, isopropyl, n-butyl, isobutyl, sec-butyl, t-butyl, pentyl, isoamyl, n-hexyl, etc., but does not limited thereto. The term "aliphatic" radical means alkenyl, alkynyl or alkyl.

Preferable compounds among the compound of formula (1) include those wherein $R_1$ represents 3-pyridyl, $R_2$ and $R_3$ each represent hydrogen, $R_6$ or $R_7$ represents a radical having the following formula (2):

$$\text{—} \underset{H}{N} \text{—} \overset{O}{\underset{\|}{C}} \text{—} \bigcirc \text{—} \underset{H_2}{C} \text{—} (X)_n \text{—} R_9 \tag{2}$$

wherein X represents NH, n=0 or 1, and $R_9$ represents piperidine, 4-methylhomopiperazine, or 4-methylpiperazine, and $R_4$, $R_5$, $R_7$, and $R_8$ each represent hydrogen, or one or two thereof each represent fluoro, methyl, or methoxy when $R_6$ represents the radical of the above formula (2), or one or two of $R_4$, $R_5$, $R_6$, and $R_8$ each represent fluoro, methyl, or methoxy when $R_7$ represents the radical of the above formula (2).

In the aspect of inhibition of protein kinase, particularly preferable compounds among the compound of formula (1) include those wherein $R_1$ represents 3-pyridyl, $R_2$, $R_3$, $R_4$, $R_5$, $R_7$, and $R_8$ each represent hydrogen, and $R_6$ represents the radical of formula (2) wherein n=0 and $R_9$ represents 4-methylhomopiperazine, or n=1, X represents NH, and $R_9$ represents 4-methylpiperazine.

Further, the compound of formula (1) wherein $R_1$ represents 3-pyridyl, $R_2$ and $R_3$ each represent hydrogen, $R_4$ represents methyl, $R_5$, $R_6$ and $R_8$ each represent hydrogen, and $R_7$ represents the radical of formula (2) wherein n=1, X represents NH, and $R_9$ represents 4-methylpiperazine is particularly preferable.

The compound of formula (1) includes one or more basic groups or one or more basic radicals, and so may form an acid addition salt with aliphatic sulfonic acid (i.e., methanesulfonic acid, ethanesulfonic acid), hydrochloric acid, sulfuric acid, phosphoric acid, trifluoroacetic acid, acetic acid, propionic acid, glycolic acid, succinic acid, maleic acid, fumaric acid, citric acid, tartaric acid, oxalic acid, amino acid (i.e., lysine), benzoic acid, salicylic acid, etc. When several basic groups exist in a molecule, the compound of formula (1) may form mono or poly acid addition salt. Among the pharmaceutically acceptable salts as mentioned above, acetic acid salt and hydrochloric acid salt are better than methanesulfonic acid salt, since they have better solubility in water and show good absorptivity in Pk test.

According to the present invention, the compound of formula (1) as defined above and its salt can be prepared by a process which comprises reacting a compound represented by the following formula (3a) or (3b):

(3a)

(3b)

wherein $R_1$ to $R_8$ are as defined above, with a compound represented by the following formula (4):

(4)

wherein L represents a leaving group, preferably halogen, to produce a compound represented by the following formula (5a) or (5b):

(5a)

(5b)

wherein $R_1$ to $R_8$ and L are as defined above, and reacting the compound of formula (5a) or (5b) with a compound represented by the following formula (6):

$$H(X)_n\text{—}R_9,\quad (6)$$

wherein X, n, and $R_9$ are as defined above, to give a compound represented by the following formula (1a) or (1b):

(1a)

(1b)

wherein $R_1$ to $R_8$, X, n, and $R_9$ are as defined above. Therefore, it is another purpose of the present invention to provide the above process.

The above process according to the present invention is preferably carried out in a solvent and in the presence of a base. Any conventional solvent or base which does not adversely affect the reaction can be used, but one or more solvents selected from a group consisting of tetrahydrofuran, methylene chloride, ethanol, and methanol, and one or more bases selected from a group consisting of pyridine and triethylamine can be preferably mentioned.

Typical examples of the above process are depicted in the following Reaction Schemes 1 and 2. Any person skilled in the art can easily prepare the other compounds by referring to the specific examples.

Reaction Scheme 1

-continued

Reaction Scheme 2

The starting materials used in Reaction Schemes 1 and 2 are commercially available and can be easily obtained. The reaction may be conventionally carried out under cooling to warming. After the reaction is completed, the resulting product may be further purified by usual work-up processes, for example, column chromatography, recrystallization, etc.

The above process for preparing the compound of formula (1) of the present invention gives such advantages as stability of the chemical structure of the intermediates, simple control of reaction conditions, increase of the reaction yield, etc. when compared with the known process comprising the steps of coupling the compound of formula (4) with the compound of formula (6) first, and then reacting the resulting compound with the compound of formula (3a) or (3b).

The compound of formula (1) of the present invention exhibits a superior effect on lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer etc., and so can be advantageously used for the treatment of those diseases. Particularly, the compound of formula (1) wherein X is NH shows better medicinal effect on CML than Imatinib mesylate, and the compound of formula (1) wherein the substituent of formula (2) is introduced into the position of $R_6$ shows an excellent anti-cancer activity on several parts of the body including lung, stomach, etc. Further, if the salt form of the compound of formula (1) is converted from methanesulfonate to acetate or hydrochloride, water solubility and absorptivity into the body of animals are highly increased. The effect of the compound of formula (1) and its salt according to the present invention can be confirmed by the test results of the following experiments.

When the active compound according to the present invention is used for clinical purpose, it is preferably administered in an amount ranging generally from 1 to 100 mg, preferably from 3 to 6 mg per kg of body weight a day. The total daily dosage may be administered once or over several times. However, the specific administration dosage for a patient can be varied with the specific compound used, body weight, sex or hygienic condition of the subject patient, diet, time or method of administration, excretion rate, mixing ratio of the agent, severity of the disease to be treated, etc.

The compound of the present invention may be administered in the form of injections or oral preparations.

Injections, for example, sterilized aqueous or oily suspension for injection, can be prepared according to the known procedure using suitable dispersing agent, wetting agent, or suspending agent. Solvents which can be used for preparing injections include water, Ringer's fluid, and isotonic NaCl solution, and also sterilized fixing oil may be conveniently used as solvent or suspending media. Any non-stimulative fixing oil including mono- or di-glyceride may be used for this purpose. Fatty acid such as oleic acid may also be used for injections.

As the solid preparations for oral administration, capsules, tablets, pills, powders, granules, etc., preferably capsules and tablets can be mentioned. It is also desirable for tablets and pills to be formulated into enteric-coated preparations. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent, and binding agent.

When the compound according to the present invention is clinically applied for the treatment of lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer etc., the active compound of formula (1) can be administered alone or in combination with the existing chemotherapeutic agents such as 5-Fu, cisplatin, taxol, methotrexate, anthracyclin, etc.

The present invention will be more specifically explained in the following Examples and Experiments. However, it should be understood that these Examples and Experiments are intended to illustrate the present invention but not in any manner to limit the scope of the present invention. In the following Examples, $R_f$ value was measured on silica gel (Merck, 60F254, Germany); the ratio of each solvent in the eluent mixture was volume ratio (v/v); and melting point was measured by DSC thermoanalysis instrument (NETZSCH, DSC204 cell). $^1$H-NMR was measured by Brucker, Ac-200.

EXAMPLES

Preparation 1

N-(2-methyl-5-nitrophenyl)-4-(3-pyridyl)-2-pyrimidine-amine (35 g, 0.114 mol) and stannous chloride dihydrate (128.5 g, 0.569 mol) were dissolved in a solvent mixture of ethyl acetate and ethanol (250 ml, 10/1, v/v), and the reaction solution was refluxed for 4 hours. The solution was cooled to room temperature, washed with 10% aqueous sodium hydroxide solution, and concentrated to give N-(5-amino-2-methylphenyl)-4-(3-pyridyl)-2-pyrimidine-amine (35 g).

$R_f$=0.45 (Methylene chloride:Methanol=9:1)
$^1$H-NMR (DMSO-$d_6$)=2.04 (s, 3H), 6.30-6.34 (m, 1H), 6.76-6.77 (m, 1H), 6.84-6.87 (d, 1H), 7.34-7.35 (m, 1H), 7.50-7.56 (m, 1H), 8.38-8.47 (m, 1H), 8.53-8.57 (m, 2H), 8.66-8.70 (m, 1H), 9.23-9.24 (d, 1H)

The starting material was prepared as follows.
Step 1.1
3-Acetylpyridine (100 g, 0.19 mol) was added to dimethylformamide dimethylacetal (156.5 g, 1.27 mol), and the mixture was reacted under reflux for 23 hours. After the reaction mixture was cooled to 0° C., a mixture of diethyl ether and hexane (3:2, v/v) (500 ml) was added and the whole mixture was stirred for 4 hours. The resulting solid was filtered and washed with a mixture of diethyl ether and hexane (500 ml, 3/2, v/v) to give 3-dimethylamino-1-(3-pyridyl)-2-propen-1-one (120 g).

$R_f$=0.46 (Methylene chloride:Methanol=9:1)
$^1$H-NMR (CDCl$_3$)=3.04 (s, 3H), 3.24 (s, 3H), 5.83 (s, 1H), 5.89 (s, 1H), 7.48-7.55 (m, 1H), 7.89-7.95 (m, 1H), 8.27-8.32 (m, 1H), 9.00-9.02 (s, 1H)

Step 1.2
2-Methyl-5-nitroaniline (100 g, 0.657 mol) was dissolved in ethanol (250 ml), and 65% aqueous nitric acid solution (48 ml, 0.65 mol) was added thereto. When the exothermic reaction was stopped, cyanamide (41.4 g) dissolved in water (41.4 g) was added thereto. The brown mixture was reacted under reflux for 24 hours. The reaction mixture was cooled to 0° C., filtered, and washed with ethanol:diethyl ether (1:1, v/v) to give 2-methyl-5-nitrophenyl-guanidine nitrate (98 g).

$R_f$=0.1 (Methylene chloride:Methanol: 25% Aqueous ammonia=150:10:1)
$^1$H-NMR (DMSO-$d_6$)=1.43 (s, 3H), 6.59 (s, 3H), 6.72-6.76 (d, 1H), 7.21-7.27 (m, 1H), 8.63-8.64 (br, 1H)

Step 1.3
3-Dimethylamino-1-(3-pyridyl)-2-propen-1-one (25 g, 0.14 mol), 2-methyl-5-nitrophenyl-guanidine nitrate (36 g, 0.14 mol), and sodium hydroxide (6.5 g, 0.163 mol) were dissolved in isopropanol and reacted under reflux for 18 hours. The reaction solution was cooled to 0° C., filtered, washed with isopropanol and methanol, and dried to give N-(2-methyl-5-nitrophenyl)-4-(3-pyridyl)-2-pyrimidine-amine (20 g).

$R_f$=0.6 (Methylene chloride:Methanol=9:1)
$^1$H-NMR (DMSO-$d_6$)=2.43 (s, 3H), 7.50-7.60 (m, 2H), 7.89-7.93 (m, 1H), 8.47-8.50 (m, 1H), 8.62-8.64 (m, 1H), 8.71-8.74 (m, 1H), 8.78-8.81 (m, 1H), 9.27-9.33 (m, 2H)

Preparation 2

N-(5-amino-2-methylphenyl)-4-(3-pyridyl)-2-pyrimidine-amine (2.83 g, 8.29 mmol) was dissolved in tetrahydrofuran (20 ml), triethylamine (1.4 ml, 9.95 mmol) was added thereto, and the mixture was stirred for 30 minutes. 4-Chloromethyl benzoyl chloride (2.03 g, 10.78 mmol) was added and the whole mixture was reacted under reflux for 4 hours. The mixture was filtered, and the filtrate was concentrated and crystallized from water to give N-(5-(4-chloromethyl-benzoylamino)-2-methylphenyl)-4-(3-pyridyl)-2-pyrimidine-amine (3.12 g).

$R_f$=0.38 (Methylene chloride:Methanol=9:1)
$^1$H-NMR (DMSO-$d_6$)=2.23 (s, 3H), 4.45 (s, 2H), 7.20-7.24 (d, 1H), 7.43-7.61 (m, 5H), 7.94-7.98 (d, 1H), 8.09 (s, 1H), 8.50-8.53 (d, 1H), 9.02 (s, 1H), 9.28 (s, 1H), 10.27 (s, 1H)

Example 1

N-(5-(4-chloromethylbenzoylamino)-2-methylphenyl)-4-(3-pyridyl)-2-pyrimidine-amine (1 g, 2.33 mmol) was dissolved in tetrahydrofuran (20 ml), pyridine (360 ml, 4.66 mmol) was added thereto, and the mixture was stirred for 30 minutes. N-methylhomopiperazine (434 µl, 3.49 mmol) was added thereto, and the mixture was refluxed for 12 hours and filtered. The filtrate was concentrated, subjected to column chromatography (eluent: chloroform:methanol=3:1(v/v)), concentrated again, and then crystallized from dimethylether to give 4-(4-methylhomopiperazin-1-ylmethyl)-N-[4-methyl-3-(4-(pyridin-3-yl)pyrimidin-2-yl)aminophenyl]benzamide (0.71 g).

$R_f$=0.41 (Chloroform:Methanol=1:1)
$^1$H-NMR (DMSO-$d_6$)=1.73-1.76 (m, 2H), 2.31 (s, 3H), 2.33 (s, 3H), 2.61-2.70 (m, 8H), 3.69 (1s, 2H), 7.08 (d, 1H), 7.36-7.56 (m, 7H), 7.93-7.97 (d, 2H), 8.29 (s, 1H), 8.58-8.76 (m, 3H), 9.37 (s, 1H), 10.17 (s, 1H)

Example 2

4-(4-Methylhomopiperazin-1-ylmethyl)-N-[4-methyl-3-(4-(pyridin-3-yl)pyrimidin-2-yl)aminophenyl]benzamide (250 mg, 0.429 mmol) was dissolved in ethanol (10 ml), methanesulfonic acid (64 µl, 0.984 mmol) was added, and the mixture was reacted at room temperature for 16 hours. The resulting solid was filtered and washed with acetone to give 4-(4-methylhomopiperazin-1-ylmethyl)-N-[4-methyl-3-(4-(pyridin-3-yl)pyrimidin-2-yl)aminophenyl]benzamide methanesulfonate (230 mg).

$R_f$=0.2 (Methylene chloride:Methanol: 25% Aqueous ammonia=150:10:1)
mp=166-168° C.
$^1$H-NMR (DMSO-$d_6$)=2.12 (br, 2H), 2.58 (s, 3H), 2.65 (s, 3H), 2.80 (s, 3H), 3.37 (m, 4H), 3.62 (m, 4H), 4.33 (s, 2H), 7.05 (d, 1H), 7.16 (s, 3H), 7.41-7.43 (d, 2H), 7.67-7.79 (m, 3H), 8.15 (d, 1H), 8.49 (d, 1H), 8.64 (d, 1H), 8.91 (s, 1H)

Example 3

N-[5-(4-chloromethylbenzoylamino)-2-methylphenyl]-4-(3-pyridyl)-2-pyrimidine-amine (1 g, 2.33 mmol) was dissolved in tetrahydrofuran (20 ml), pyridine (360 µl, 4.66 mmol) was added thereto, and the mixture was stirred for 30 minutes. 1-Amino-4-methylpiperazine (418 µl, 3.49 mmol) was added, and the mixture was refluxed for 12 hours and filtered. The filtrate was concentrated, subjected to column chromatography (eluent: chloroform:methanol=3:1(v/v)), concentrated again, and then crystallized from dimethylether to give 4-(4-methylpiperazin-1-ylaminomethyl)-N-[4-methyl-3-(4-(pyridin-3-yl)pyrimidin-2-yl)aminophenyl]benzamide (880 mg).

$R_f$=0.40 (Chloroform:Methanol=1:1)
$^1$H-NMR (CDCl$_3$)=2.31 (d, 6H), 7.48 (br, 8H), 3.54 (s, 2H), 7.06-7.42 (m, 8H), 7.79-7.83 (d, 2H), 8.07 (s, 1H), 8.46-8.68 (m, 4H), 9.20 (m, 1H)

Example 4

4-(4-Methylpiperazin-1-ylaminomethyl)-N-[4-methyl-3-(4-(pyridin-3-yl)pyrimidin-2-yl)aminophenyl]benzamide (95 mg, 0.187 mmol) was dissolved in ethanol (8 ml), methanesulfonic acid (24 µl, 0.347 mmol) was added thereto, and the mixture was reacted at room temperature for 16 hours. The resulting solid was filtered and washed with acetone to give 4-(4-methylpiperazin-N-ylaminomethyl)-N-[4-methyl-3-(4-(pyridin-3-yl)pyrimidin-2-yl)aminophenyl]benzamide methanesulfonate (80 mg).

$R_f$=0.2 (Methylene chloride:Methanol: 25% Aqueous ammonia=150:10:1)
mp=144-146° C.
$^1$H-NMR (D$_2$O)=1.79 (s, 3H), 2.67 (s, 3H), 2.78-2.81 (m, 8H), 3.22 (s, 3H), 3.67 (s, 2H), 6.62 (d, 1H), 6.75-6.81 (m, 2H), 7.18-7.22 (m, 3H), 7.36-7.40 (d, 2H), 7.74 (s, 1H), 7.86-7.89 (d, 1H), 8.15-8.18 (d, 2H), 8.60 (s, 1H)

Preparation 3

N-(4-methyl-3-nitrophenyl)-4-(3-pyridyl)-2-pyrimidine-amine (34 g, 0.11 mol) and stannous chloride dihydrate (124.5 g, 0.55 mol) were dissolved in a solvent mixture of ethyl acetate and ethanol (300 ml, 10/1, v/v) and reacted under reflux for 26 hours. The reaction mixture was cooled to room temperature, washed with 10% aqueous hydrochloric acid solution, concentrated, and subjected to column chromatography (chloroform/methanol=9/1, v/v) to give N-(3-amino-4-methylphenyl)-4-(3-pyridyl)-2-pyrimidine-amine (32 g).

$R_f$=0.48 (Methylene chloride:Methanol=9:1)
$^1$H-NMR (DMSO-d$_6$)=2.20 (s, 3H), 4.81 (s, 2H), 6.81-6.94 (m, 2H), 7.08 (s, 1H), 7.40-7.43 (d, 1H), 7.54-7.61 (m, 1H), 8.48-8.55 (m, 2H), 8.71-8.76 (m, 1H), 9.33-9.40 (d, 1H)

The starting material was prepared as follows.

Step 3.1

4-Methyl-3-nitroaniline (90 g, 0.592 mol) was dissolved in ethanol (250 ml) and 65% aqueous nitric acid solution (59 g, 0.592 mol) was added thereto. When the exothermic reaction is stopped, cyanamide (74.6 g) dissolved in water in a concentration of 50% was added. The brown mixture was reacted under reflux for 24 hours. The reaction mixture was cooled to 0° C., filtered, and washed with diethylether to give 4-methyl-3-nitrophenyl-guanidine nitrate (93 g).

$R_f$=0.1 (Methylene chloride:Methanol: 25% Aqueous ammonia=150:10:1)
$^1$H-NMR (DMSO-d$_6$)=2.50 (s, 3H), 7.48-7.56 (m, 2H), 7.86 (s, 1H), 8.11-8.15 (d, 2H)

Step 3.2

3-Dimethylamino-1-(3-pyridyl)-2-propen-1-one (20 g, 0.1 µmol), 4-methyl-3-nitrophenyl-guanidine nitrate (32 g, 0.12 mol), and sodium hydroxide (6.8 g, 0.17 mol) were dissolved in isopropanol, and reacted under reflux for 28 hours. The reaction solution was cooled to 0° C., filtered, washed with isopropanol, water and ethanol, and dried to give N-(4-methyl-3-nitrophenyl)-4-(3-pyridyl)-2-pyrimidine-amine (32 g).

$R_f$=0.76 (Methylene chloride:Methanol=9:1)
$^1$H-NMR (DMSO-d$_6$)=2.43 (s, 3H), 7.44-7.47 (d, 1H), 7.61-7.63 (d, 2H), 7.89-7.94 (d, 1H), 8.55-8.59 (d, 1H), 8.69-8.71 (d, 1H), 8.77-8.79 (m, 1H), 8.86 (s, 1H), 9.41 (s, 1H)

Preparation 4

N-(3-amino-4-methylphenyl)-4-(3-pyridyl)-2-pyrimidine-amine (11 g, 39.8 mmol) was dissolved in tetrahydrofuran (100 ml), triethylamine (8.3 ml, 59.5 mmol) was added thereto, and the mixture was stirred for 30 minutes. 4-Chloromethyl benzoyl chloride (2.03 g, 10.78 mmol) was added, and the resulting mixture was reacted under reflux for 2 hours. The reaction mixture was filtered, and the filtrate was concentrated and crystallized from methylene chloride to give N-(5-(4-chloromethylbenzoylamino)-4-methylphenyl)-4-(3-pyridyl)-2-pyrimidine-amine (5.3 g).

$R_f$=0.86 (Methylene chloride:Methanol=9:1)
$^1$H-NMR (DMSO-d$_6$)=2.23 (s, 3H), 4.89 (s, 2H), 7.23-7.27 (d, 1H), 7.52-7.66 (m, 5H), 8.02-8.08 (m, 3H), 8.57-8.65 (m, 1H), 8.75-8.77 (d, 1H), 9.40 (s, 1H), 9.83 (s, 1H), 9.99 (s, 1H)

Example 5

N-(5-(4-chloromethylbenzoylamino)-4-methylphenyl)-4-(3-pyridyl)-2-pyrimidine-amine (1.5 g, 3.49 mmol) was dissolved in tetrahydrofuran (30 ml), pyridine (560 µl, 6.98 mmol) was added, and the mixture was stirred for 30 minutes. N-methylhomopiperazine (660 µl, 5.23 mmol) was added thereto, and the resulting mixture was refluxed for 12 hours and then filtered. The filtrate was concentrated and crystallized from dimethylether to give 4-(4-methylhomopiperazin-1-ylmethyl)-N-[2-methyl-5-(4-(pyridin-3-yl)pyrimidin-2-yl)aminophenyl]benzamide (1.2 g).

$R_f$=0.12 (Chloroform:Methanol=1:1)
$^1$H-NMR (DMSO-d$_6$)=1.98-2.03 (m, 2H), 2.33 (s, 3H), 2.47-2.99 (m, 8H), 3.15 (s, 3H), 4.27 (s, 2H), 7.16-7.19 (m, 3H), 7.23-7.26 (d, 1H), 7.41-7.53 (m, 4H), 7.79-7.89 (m, 3H), 8.44-8.53 (m, 2H), 8.70-8.72 (d, 1H), 9.27 (s, 1H)

Example 6

4-(4-Methylhomopiperazin-1-ylmethyl)-N-[2-methyl-5-(4-(pyridin-3-yl)pyrimidin-2-yl)aminophenyl]benzamide (1.2 g, 2.29 mmol) was dissolved in ethanol (18 ml), methanesulfonic acid (149 µl, 2.29 mmol) was added, and the mixture was reacted at room temperature for 18 hours. The resulting solid was filtered and washed with acetone to give 4-(4-methylhomopiperazin-1-ylmethyl)-N-[2-methyl-5-(4-(pyridin-3-yl)pyrimidin-2-yl)aminophenyl]benzamide methanesulfonate (1.03 g).

$R_f$=0.2 (Methylene chloride:Methanol: 25% Aqueous ammonia=150:10:1)
mp=168-170° C.
$^1$H-NMR (D$_2$O)=2.14 (m, 2H), 2.67 (d, 6H), 2.88 (s, 3H), 3.23-3.51 (m, 8H), 3.70 (s, 2H), 7.25-7.34 (m, 3H), 7.46 (s, 1H), 7.57-7.90 (m, 6H), 8.70-8.74 (m, 1H), 8.98-9.01 (m, 1H), 9.24 (s, 1H)

Example 7

N-(5-(4-chloromethylbenzoylamino)-4-methylphenyl)-4-(3-pyridyl)-2-pyrimidine-amine (1.5 g, 3.49 mmol) was dissolved in tetrahydrofuran (30 ml), pyridine (560 μl, 6.98 mmol) was added, and the mixture was stirred for 30 minutes. 1-Amino-4-methylpiperazine (580 μl, 5.23 mmol) was added thereto, and the resulting mixture was refluxed for 12 hours and then filtered. The filtrate was concentrated and crystallized from dimethylether to give 4-(4-methylpiperazin-1-ylaminomethyl)-N-[2-methyl-5-(4-(pyridin-3-yl)pyrimidin-2-yl)aminophenyl]benzamide (1.7 g).

$R_f$=0.39 (Chloroform:Methanol=1:1)

$^1$H-NMR (DMSO-$d_6$)=2.22 (d, 6H), 2.53 (m, 8H), 3.42 (s, 2H), 7.21-7.26 (m, 1H), 7.46-7.64 (m, 7H), 7.98-8.02 (d, 2H), 8.57-8.63 (m, 3H), 8.73-8.75 (d, 1H), 9.39 (s, 1H), 9.82-9.92 (d, 1H)

Example 8

4-(4-Methylpiperazin-1-ylaminomethyl)-N-[2-methyl-5-(4-(pyridin-3-yl)pyrimidin-2-yl)aminophenyl]benzamide (1.7 g, 3.42 mmol) was dissolved in ethanol (25 ml), methanesulfonic acid (222 μl, 3.42 mmol) was added, and the mixture was reacted at room temperature for 18 hours. The resulting solid was filtered and washed with acetone to give 4-(4-methylpiperazin-1-ylaminomethyl)-N-[2-methyl-5-(4-(pyridin-3-yl)pyrimidin-2-yl)aminophenyl]benzamide methanesulfonate (1.43 g).

$R_f$=0.17 (Methylene chloride:Methanol: 25% Aqueous ammonia=150:10:1)

mp=150-152° C.

$^1$H-NMR ($D_2O$)=2.12 (s, 3H), 2.66 (d, 6H), 2.92 (s, 3H), 3.59 (m, 8H), 4.46 (s, 2H), 7.16-7.27 (m, 2H), 7.33-7.35 (d, 1H), 7.43 (s, 1H), 7.50-7.62 (d, 2H), 7.89-8.03 (m, 3H), 8.33-8.36 (d, 1H), 8.72-8.75 (d, 1H), 8.98-9.02 (d, 1H), 9.23 (s, 1H)

Preparation 5

N-(4-nitrophenyl)-4-(3-pyridyl)-2-pyrimidine-amine was reacted according to the same procedure as Preparation 1 to give N-(4-aminophenyl)-4-(3-pyridyl)-2-pyrimidine-amine (7.1 g).

$R_f$=0.5 (Chloroform:Methanol=9:1)

$^1$H-NMR (DMSO-$d_6$)=4.84 (s, 2H), 6.55-6.59 (d, 2H), 7.34-7.41 (t, 3H), 7.54-7.61 (m, 1H), 8.44-8.50 (m, 2H), 8.70-8.73 (m, 1H), 9.27-9.31 (m, 2H)

Step 5.1

4-Nitroaniline (30 g, 0.22 mol) and cyanamide (water 50%) (27.4 g, 0.33 mol) were reacted according to the same procedure as Step 1.2 of Preparation 1 to give 4-nitrophenyl-guanidine nitrate (29.1 g).

$R_f$=0.1 (Methylene chloride:Methanol: 25% Aqueous ammonia=150:10:1)

$^1$H-NMR (DMSO-$d_6$)=7.46-7.50 (d, 2H), 7.90 (br, 4H), 8.28-8.32 (d, 2H)

Step 5.2

4-Nitrophenyl-guanidine nitrate (20 g, 0.08 mol) and 3-dimethylamino-1-(3-pyridyl)-2-propen-1-one (11.75 g, 0.06 mol) were reacted according to the same procedure as Step 1.3 of Preparation 1 to give N-(4-nitrophenyl)-4-(3-pyridyl)-2-pyrimidine-amine (9.38 g).

$R_f$=0.7 (Chloroform:Methanol=9:1)

$^1$H-NMR (DMSO-$d_6$)=7.59-7.62 (m, 1H), 7.72 (d, 1H), 8.07-8.12 (d, 2H), 8.24-8.28 (d, 2H), 8.54-8.58 (m, 1H), 8.73-8.77 (m, 2H), 9.38 (s, 1H), 10.62 (s, 1H)

Preparation 6

4-(Chloromethyl)benzoylchloride (10 g, 53 mmol) was reacted according to the same procedure as Preparation 2 to give N-(4-(4-chloromethylbenzoylamino)phenyl)-4-(3-pyridyl)-2-pyrimidine-amine (13.2 g).

$R_f$=0.6 (Chloroform:Methanol=9:1)

$^1$H-NMR (DMSO-$d_6$)=4.88 (s, 2H), 7.45-7.511 (m, 3H), 7.55-7.64 (m, 1H), 7.71-7.73 (m, 4H), 7.85-7.89 (m, 2H), 8.43-8.55 (m, 2H), 8.71 (d, 1H), 9.30 (s, 1H), 9.71 (s, 1H), 10.03 (s, 1H)

Example 9

1-Methylhomopiperazine (3.45 g, 30.2 mmol) was reacted according to the same procedure as Example 1 to give 4-(4-methylhomopiperazin-1-ylmethyl)-N-[4-(4-(pyridin-3-yl)pyrimidin-2-yl)aminophenyl]benzamide (3.7 g).

$R_f$=0.4 (Chloroform:Methanol=1:1)

$^1$H-NMR (DMSO-$d_6$)=1.69-1.74 (m, 2H), 2.24 (s, 3H), 2.45-2.67 (m, 8H), 3.67 (s, 2H), 7.43-7.50 (m, 3H), 7.56-7.63 (m, 1H), 7.74-7.77 (m, 4H), 7.89-7.93 (m, 2H), 8.49-8.61 (m, 2H), 8.73 (d, 1H), 9.34 (s, 1H), 9.76 (s, 1H), 10.16 (s, 1H)

Example 10

Methanesulfonic acid (0.58 g, 6 mmol) was reacted according to the same procedure as Example 2 to give 4-(4-methylhomopiperazin-1-ylmethyl)-N-[4-(4-(pyridin-3-yl)pyrimidin-2-yl)aminophenyl]benzamide methanesulfonate (1.47 g).

$R_f$=0.2 (Methylene chloride:Methanol: 25% Aqueous ammonia=150:10:1)

mp=152-154° C.

$^1$H-NMR ($D_2O$)=1.69 (m, 2H), 2.67 (s, 3H), 2.81 (s, 3H), 3.05 (m, 2H), 3.28-3.44 (m, 6H), 3.96 (s, 2H), 6.93-6.96 (m, 1H), 7.16-7.38 (m, 7H), 7.60-7.64 (m, 2H), 8.11-8.13 (m, 2H), 8.40 (m, 1H), 8.70 (s, 1H)

Preparation 7

N-(3-nitrophenyl)-4-(3-pyridyl)-2-pyrimidine-amine (24 g, 0.08 mol) was reacted according to the same procedure as Preparation 1 to give N-(3-aminophenyl)-4-(3-pyridyl)-2-pyrimidine-amine (15.5 g).

$R_f$=0.5 (Chloroform:Methanol=9:1)

$^1$H-NMR (DMSO-$d_6$)=5.03 (s, 2H), 6.22-6.23 (m, 1H), 6.89-6.96 (m, 2H), 7.08 (s, 1H), 7.45 (d, 1H), 7.55-7.62 (m, 1H), 8.49-8.58 (m, 2H), 8.72-8.74 (m, 1H), 9.34 (s, 1H), 9.47 (s, 1H)

Step 7.1

3-Nitroaniline (42 g, 0.3 mol) and cyanamide (water 50%) (38.4 g, 0.46 mol) were reacted according to the same procedure as Step 1.2 of Preparation 1 to give 3-nitrophenyl-guanidine nitrate (33.4 g).

$R_f$=0.1 (Methylene chloride:Methanol: 25% Aqueous ammonia=150:10:1)

$^1$H-NMR (DMSO-$d_6$)=7.75-7.81 (m, 5H), 8.14-8.17 (d, 2H)

Step 7.2

3-Nitrophenyl-guanidine nitrate (28 g, 0.12 mol) and 3-dimethylamino-1-(3-pyridyl)-2-propen-1-one (16.9 g, 0.09 mol) were reacted according to the same procedure as Step 1.3 of Preparation 1 to give N-(3-nitrophenyl)-4-(3-pyridyl)-2-pyrimidine-amine (18.4 g).

$R_f$=0.7 (Chloroform:Methanol=9:1)

$^1$H-NMR (DMSO-$d_6$)=7.58-7.67 (m, 3H), 7.82-7.87 (m, 1H), 8.08-8.12 (m, 1H), 8.56-8.60 (m, 1H), 8.71-8.78 (m, 2H), 9.11 (s, 1H), 9.42-9.43 (d, 1H), 10.38 (s, 1H)

Preparation 8

4-(Chloromethyl)benzoylchloride (10 g, 53 mmol) was reacted according to the same procedure as Preparation 2 to give N-[3-(4-chloromethylbenzoylamino)phenyl]-4-(3-pyridyl)-2-pyrimidine-amine (15.34 g).

$R_f$=0.6 (Chloroform:Methanol=9:1)
$^1$H-NMR (DMSO-$d_6$)=4.88 (s, 2H), 7.33 (br, 2H), 7.53-7.64 (m, 5H), 7.99-8.03 (d, 2H), 8.48 (s, 1H), 8.62-8.75 (m, 2H), 9.40 (s, 1H), 9.85 (s, 1H), 10.32 (s, 1H)

Example 11

1-Methylhomopiperazine (1.08 g, 9.5 mmol) was reacted according to the same procedure as Example 1 to give 4-(4-methylhomopiperazin-1-ylmethyl)-N-[3-(4-(pyridin-3-yl)pyrimidin-2-yl)aminophenyl]benzamide (2.8 g).

$R_f$=0.4 (Chloroform:Methanol=1:1)
$^1$H-NMR (DMSO-$d_6$)=1.73-1.75 (m, 2H), 2.15 (s, 3H), 2.51-2.69 (m, 8H), 3.69 (s, 2H), 7.31 (s, 2H), 7.46-7.61 (m, 6H), 7.93-7.96 (d, 2H), 8.46 (s, 1H), 8.66-8.75 (m, 2H), 9.40 (s, 1H), 9.82 (s, 1H), 10.24 (s, 1H)

Example 12

Methanesulfonic acid (0.24 g, 2.5 mmol) was reacted according to the same procedure as Example 2 to give 4-(4-methylhomopiperazin-1-ylmethyl)-N-[3-(4-(pyridin-3-yl)pyrimidin-2-yl)aminophenyl]benzamide methanesulfonate (0.78 g).

$R_f$=0.2 (Methylene chloride:Methanol: 25% Aqueous ammonia=150:10:1)
mp=206-208° C.
$^1$H-NMR ($D_2O$)=2.15-2.17 (m, 2H), 2.62 (s, 3H), 2.82 (s, 3H), 3.41-3.65 (m, 8H), 4.40 (s, 2H), 7.12-7.15 (m, 1H), 7.17-7.29 (m, 3H), 7.51-7.54 (m, 2H), 7.78-7.93 (m, 4H), 8.30-8.33 (m, 1H), 8.53 (s, 1H), 9.03 (s, 1H), 9.21 (s, 1H)

Example 13

1-Amino-4-methylpiperazine (1 g, 8.7 mmol) was reacted according to the same procedure as Example 3 to give 4-(4-methylpiperazin-1-ylaminomethyl)-N-[3-(4-(pyridin-3-yl)pyrimidin-2-yl)aminophenyl]benzamide (1.7 g).

$R_f$=0.4 (Chloroform:Methanol=1:1).
$^1$H-NMR (DMSO-$d_6$)=2.16 (s, 3H), 2.37-2.39 (m, 8H), 3.54 (s, 2H), 7.31 (m, 2H), 7.44-7.54 (m, 6H), 7.92-7.96 (m, 2H), 8.45 (br, 1H), 8.61-8.74 (m, 3H), 9.36 (s, 1H), 9.81 (s, 1H), 10.23 (s, 1H)

Example 14

Methanesulfonic acid (48 mg, 0.5 mmol) was reacted according to the same procedure as Example 4 to give 4-(4-methylpiperazin-1-ylaminomethyl)-N-[3-(4-(pyridin-3-yl)pyrimidin-2-yl)aminophenyl]benzamide methanesulfonate (0.23 g).

$R_f$=0.2 (Methylene chloride:Methanol: 25% Aqueous ammonia=150:10:1)
mp=148-150° C.
$^1$H-NMR ($D_2O$)=2.68 (s, 3H), 2.89 (s, 3H), 3.42-3.51 (m, 8H), 4.36 (s, 2H), 7.10 (m, 2H), 7.32-7.38 (m, 3H), 7.54-7.57 (d, 2H), 7.86-7.93 (m, 3H), 8.00-8.08 (m, 1H), 8.46 (d, 1H), 8.75 (d, 1H), 9.07 (d, 1H), 9.32 (s, 1H)

Preparation 9

N-(2-methyl-4-nitrophenyl)-4-(3-pyridyl)-2-pyrimidine-amine (23 g, 0.075 mol) was reacted according to the same procedure as Preparation 1 to give N-(2-methyl-4-aminophenyl)-4-(3-pyridyl)-2-pyrimidine-amine (21 g).

$R_f$=0.5 (Chloroform:Methanol=9:1)
$^1$H-NMR (DMSO-$d_6$)=2.08 (s, 3H), 4.97 (s, 2H), 6.40-6.46 (m, 2H), 7.01 (d, 1H), 7.29 (d, 1H), 7.53-7.56 (m, 1H), 8.37-8.42 (m, 2H), 8.65-8.70 (m, 2H), 9.21 (s, 1H)

Step 9.1

2-Methyl-4-nitroaniline (90 g, 0.59 mol) and cyanamide (water 50%) (74.6 g, 0.88 mol) were reacted according to the same procedure as Step 1.2 of Preparation 1 to give 2-methyl-4-nitrophenyl-guanidine nitrate (95 g).

$R_f$=0.1 (Methylene chloride:Methanol: 25% Aqueous ammonia=150:10:1)
$^1$H-NMR (DMSO-$d_6$)=2.43 (s, 3H), 7.43-7.55 (m, 2H), 7.77 (s, 1H), 8.21-8.25 (d, 2H)

Step 9.2

2-Methyl-4-nitrophenyl-guanidine nitrate (26.3 g, 0.1 mol) and 3-dimethylamino-1-(3-pyridyl)-2-propen-1-one (15 g, 0.08 mol) were reacted according to the same procedure as Step 1.3 of Preparation 1 to give N-(2-methyl-4-nitrophenyl)-4-(3-pyridyl)-2-pyrimidine-amine (15 g).

$R_f$=0.7 (Chloroform:Methanol=9:1)
$^1$H-NMR (DMSO-$d_6$)=2.44 (s, 3H), 7.58-7.66 (m, 2H), 8.16-8.19 (m, 3H), 8.48 (d, 1H), 8.65-8.74 (m, 2H), 9.31-9.32 (m, 2H)

Preparation 10

4-(Chloromethyl)benzoylchloride (10 g, 0.053 mol) was reacted according to the same procedure as Preparation 2 to give N-(4-(4-chloromethylbenzoylamino)-2-methylphenyl)-4-(3-pyridyl)-2-pyrimidine-amine (7 g).

$R_f$=0.6 (Chloroform:Methanol=9:1)
$^1$H-NMR (DMSO-$d_6$)=2.44 (s,3H), 5.04 (s, 2H), 7.58-7.86 (m, 7H), 8.15 (d, 2H), 8.57 (d, 1H), 8.61 (d, 1H), 8.69 (d, 1H), 8.88 (s, 1H), 9.43 (s, 1H), 10.43 (s, 1H)

Example 15

1-Methylhomopiperazine (1 g, 9.5 mmol) was reacted according to the same procedure as Example 1 to give 4-(4-methylhomopiperazin-1-ylmethyl)-N-[3-methyl-4-(4-(pyridin-3-yl)pyrimidin-2-yl)aminophenyl]benzamide (2.31 g).

$R_f$=0.4 (Chloroform:Methanol=1:1)
$^1$H-NMR (DMSO-$d_6$)=1.81-1.84 (m, 2H), 2.25 (s, 3H), 2.45 (s, 3H), 2.67-2.84 (m, 8H), 3.71 (s, 2H), 7.40-7.92 (m, 7H), 7.93-7.96 (d, 2H), 8.48-8.51 (m, 2H), 8.69 (d, 1H), 8.98 (s, 1H), 9.25 (s, 1H), 10.19 (s, 1H)

Example 16

Methanesulfonic acid (0.24 g, 2.5 mmol) was reacted according to the same procedure as Example 2 to give 4-(4-methylhomopiperazin-1-ylmethyl)-N-[3-methyl-4-(4-(pyridin-3-yl)pyrimidin-2-yl)aminophenyl]benzamide methanesulfonate (0.63 g).

$R_f$=0.2 (Methylene chloride:Methanol: 25% Aqueous ammonia=150:10:1)
mp=166-168° C.
$^1$H-NMR ($D_2O$)=1.97 (s, 3H), 2.10-2.17 (m, 2H), 2.68 (s, 3H), 2.79 (s, 3H), 2.95 (m, 2H), 3.17 (m, 2H), 3.33-3.38 (m, 4H), 3.86 (s, 2H), 6.85 (d, 1H), 7.10 (m, 2H), 7.23-7.32 (m, 4H), 7.55 (d, 2H), 8.03-8.06 (m, 2H), 8.37 (d, 1H), 8.63 (s, 1H)

Example 17

1-Amino-4-methylpiperazine (1 g, 9 mmol) was reacted according to the same procedure as Example 3 to give 4-(4- methylpiperazin-1-ylaminomethyl)-N-[3-methyl-4-(4-(pyridin-3-yl)pyrimidin-2-yl)aminophenyl]benzamide (1.2 g).

$R_f$=0.4 (Chloroform:Methanol=1:1)

$^1$H-NMR (DMSO-d$_6$)=2.15 (s, 3H), 2.25 (s, 3H), 2.36 (m, 8H), 3.53 (s, 2H), 7.40-7.68 (m, 7H), 7.91-7.95 (m, 3H), 8.39-8.60 (m, 2H), 8.69-8.71 (m, 1H), 8.98 (s, 1H), 9.26 (s, 1H), 10.18 (s, 1H)

Example 18

Methanesulfonic acid (48 mg, 0.5 mmol) was reacted according to the same procedure as Example 4 to give 4-(4-methylpiperazin-1-ylaminomethyl)-N-[3-methyl-4-(4-(pyridin-3-yl)pyrimidin-2-yl)aminophenyl]benzamide methanesulfonate (0.17 g).

$R_f$=0.2 (Methylene chloride:Methanol: 25% Aqueous ammonia=150:10:1)

mp=172-174° C.

$^1$H-NMR (D$_2$O)=1.19 (s, 3H), 2.65 (s, 3H), 2.67 (s, 3H), 2.85-2.88 (m, 4H), 3.01-3.11 (m, 4H), 3.45 (s, 2H), 6.77 (d, 1H), 6.98-7.27 (m, 6H), 7.43 (d, 2H), 7.95 (m, 1H), 7.99 (d, 1H), 8.21-8.24 (m, 1H), 8.54 (s, 1H)

Preparation 11

N-(2-methoxy-5-nitrophenyl)-4-(3-pyridyl)-2-pyrimidine-amine (22 g, 0.068 mol) was reacted according to the same procedure as Preparation 1 to give N-(2-methoxy-5-aminophenyl)-4-(3-pyridyl)-2-pyrimidine-amine (10 g).

$R_f$=0.5 (Chloroform:Methanol=9:1)

$^1$H-NMR (DMSO-d$_6$)=3.74 (s, 3H), 4.75 (s, 2H), 6.24-6.28 (m, 1H), 6.75-6.80 (m, 1H), 7.48-7.60 (m, 3H), 8.01 (s, 1H), 8.50-8.58 (m, 2H), 8.72-8.74 (m, 1H), 9.34 (s, 1H)

Step 11.1

2-Methoxy-5-nitroaniline (90 g, 0.535 mol) and cyanamide (water 50%) (67.5 g, 0.803 mol) were reacted according to the same procedure as Step 1.2 of Preparation 1 to give 2-methoxy-5-nitrophenyl-guanidine nitrate (74 g).

$R_f$=0.1 (Methylene chloride: 25% Aqueous ammonia=150:10:1)

$^1$H-NMR (DMSO-d$_6$)=3.97 (s, 3H), 7.35-7.45 (m, 4H), 8.13 (m, 1H), 8.24-8.30 (m, 1H)

Step 11.2

2-Methoxy-5-nitrophenyl-guanidine nitrate (31 g, 0.113 mol) and 3-dimethylamino-1-(3-pyridyl)-2-propen-1-one (20 g, 0.113 mol) were reacted according to the same procedure as Step 1.3 of Preparation 1 to give N-(2-methoxy-5-nitrophenyl)-4-(3-pyridyl)-2-pyrimidine-amine (23 g).

$R_f$=0.7 (Chloroform:Methanol=9:1)

$^1$H-NMR (DMSO-d$_6$)=4.03 (s, 3H), 5.25 (s, 1H), 7.24 (d, 1H), 7.29 (d, 1H), 7.55-7.67 (m, 3H), 7.94-8.00 (m, 1H), 8.54 (m, 1H), 8.58-8.76 (m, 1H), 9.38 (s, 1H)

Preparation 12

4-(Chloromethyl)benzoylchloride (4.6 g, 0.053 mol) was reacted according to the same procedure as Preparation 2 to give N-[5-(4-chloromethylbenzoylamino)-2-methoxy-phenyl]-4-(3-pyridyl)-2-pyrimidine-amine (4.4 g).

$R_f$=0.6 (Chloroform:Methanol=9:1)

$^1$H-NMR (DMSO-d$_6$)=3.87 (s, 3H), 4.87 (s, 2H), 7.07 (d, 1H), 7.36-7.41 (m, 1H), 7.52-7.63 (m, 4H), 7.99 (d, 2H), 8.31 (s, 1H), 8.58-8.78 (m, 4H), 9.39 (s, 1H), 10.25 (s, 1H)

Example 19

1-Methylhomopiperazine (1.05 ml, 8.42 mmol) was reacted according to the same procedure as Example 1 to give 4-(4-methylhomopiperazin-1-ylmethyl)-N-[4-methoxy-3-(4-(pyridin-3-yl)pyrimidin-2-yl)aminophenyl]benzamide (1.1 g).

$R_f$=0.2 (Chloroform:Methanol=1:1)

$^1$H-NMR (DMSO-d$_6$)=1.74-1.83 (m, 2H), 2.30 (s, 3H), 2.66-2.74 (m, 8H), 3.69 (s, 2H), 3.87 (s, 3H), 7.07 (d, 1H), 7.35-7.56 (m, 5H), 7.94 (d, 2H), 8.29 (s, 1H), 8.58-8.76 (m, 4H), 9.38 (s, 1H), 10.17 (s, 1H)

Example 20

Methanesulfonic acid (0.18 g, 1.91 mmol) was reacted according to the same procedure as Example 2 to give 4-(4-methylhomopiperazin-1-ylmethyl)-N-[4-methoxy-3-(4-(pyridin-3-yl)pyrimidin-2-yl)aminophenyl]benzamide methanesulfonate (0.3 g).

$R_f$=0.5 (Methylene chloride:Ethyl acetate:Methanol: 25% Aqueous ammonia=60:10:30:1)

mp=140-142° C.

$^1$H-NMR (D$_2$O)=2.20 (br, 2H), 2.66 (s, 3H), 2.88 (s, 3H), 3.49 (m, 8H), 3.71 (s, 3H), 4.42 (s, 2H), 6.49 (s, 2H), 6.87-6.89 (m, 1H), 7.48-7.52 (m, 2H), 7.63-7.67 (m, 3H), 7.88-7.90 (m, 1H), 8.21 (s, 1H), 8.45 (m, 1H), 8.71 (m, 1H), 8.91 (s, 1H)

Example 21

N-[5-(4-chloromethylbenzoylamino)-2-methoxy-phenyl]-4-(3-pyridyl)-2-pyrimidine-amine (1.4 g, 3.14 mmol) and 1-amino-4-methylpiperazine (0.94 ml, 7.86 mmol) were reacted according to the same procedure as Example 3 to give 4-(4-methylpiperazin-1-yl aminomethyl)-N-[4-methoxy-3-(4-(pyridin-3-yl)pyrimidin-2-yl)aminophenyl]benzamide (0.12 g).

$R_f$=0.2 (Chloroform:Methanol=1:1)

$^1$H-NMR (DMSO-d$_6$)=2.67 (s, 3H), 2.85-2.88 (m, 8H), 3.66 (s, 2H), 3.96 (s, 3H), 6.89-6.93 (d, 2H), 7.19 (d, 1H), 7.34-7.46 (m, 4H), 7.85-7.94 (m, 4H), 8.54-8.59 (m, 1H), 8.71-8.73 (m, 1H), 8.91 (s, 1H), 9.28 (s, 1H)

Example 22

Methanesulfonic acid (0.24 g, 2.5 mmol) was reacted according to the same procedure as Example 4 to give 4-(4-methylpiperazin-1-ylaminomethyl)-N-[4-methoxy-3-(4-(pyridin-3-yl)pyrimidin-2-yl)aminophenyl]benzamide methanesulfonate (0.67 g).

$R_f$=0.5 (Methylene chloride:Ethyl acetate:Methanol: 25% Aqueous ammonia=60:10:30:1)

mp=142-144° C.

$^1$H-NMR (D$_2$O)=2.69 (s, 3H), 2.93 (s, 3H), 3.38-3.51 (m, 8H), 3.62 (s, 3H), 4.40 (s, 2H), 6.69 (br, 2H), 7.09-7.12 (m, 1H), 7.54-7.57 (m, 2H), 7.75-7.88 (m, 3H), 8.12-8.14 (m, 1H), 8.30 (s, 1H), 8.61-8.63 (m, 1H), 8.93-8.96 (m, 1H), 9.12 (s, 1H)

Preparation 13

N-(4-fluoro-3-nitrophenyl)-4-(3-pyridyl)-2-pyrimidine-amine (22 g, 0.068 mol) was reacted according to the same procedure as Preparation 1 to give N-(4-fluoro-3-aminophenyl)-4-(3-pyridyl)-2-pyrimidine-amine (14 g).

$R_f$=0.5 (Chloroform:Methanol=9:1)

$^1$H-NMR (DMSO-d$_6$)=5.12 (s, 2H), 6.91 (d, 2H), 7.22 (d, 1H), 7.43 (d, 1H), 7.54-7.61 (m, 1H), 8.48-8.56 (m, 2H), 8.70-8.73 (m, 1H), 9.32 (s, 1H), 9.51 (s, 1H)

Step 13.1

4-Fluoro-3-nitroaniline (100 g, 0.64 mol) and cyanamide (water 50%) (80.8 g, 0.96 mol) were reacted according to the same procedure as Step 1.2 of Preparation 1 to give 4-fluoro-3-nitrophenyl-guanidine nitrate (74 g).

$R_f$=0.1 (Methylene chloride:Methanol: 25% Aqueous ammonia=150:10:1)

$^1$H-NMR (DMSO-$d_6$)=7.64-7.83 (m, 6H), 8.06-8.10 (m, 1H)

Step 13.2

4-Fluoro-3-nitrophenyl-guanidine nitrate (40 g, 0.153 mol) and 3-dimethylamino-1-(3-pyridyl)-2-propen-1-one (27 g, 0.153 mol) were reacted according to the same procedure as Step 1.3 of Preparation 1 to give N-(4-fluoro-3-nitrophenyl)-4-(3-pyridyl)-2-pyrimidine-amine (30 g).

$R_f$=0.7 (Chloroform:Methanol=9:1)

$^1$H-NMR (DMSO-$d_6$)=7.23 (d, 1H), 7.51-7.63 (m, 3H), 7.78-7.99 (m, 1H), 8.52-8.73 (m, 3H), 9.41 (s, 1H), 10.28 (s, 1H)

Preparation 14

4-(Chloromethyl)benzoylchloride (4.6 g, 0.053 mol) was reacted according to the same procedure as Preparation 2 to give N-[3-(4-chloromethylbenzoylamino)-4-fluorophenyl]-4-(3-pyridyl)-2-pyrimidine-amine (3.5 g).

$R_f$=0.6 (Chloroform:Methanol=9:1)

$^1$H-NMR (DMSO-$d_6$)=4.48 (s, 2H), 7.28 (br, 2H), 7.53-7.65 (m, 4H), 8.01 (d, 2H), 8.21-8.25 (m, 1H), 8.61-8.63 (m, 2H), 8.73 (d, 1H), 9.37 (s, 1H), 9.91 (s, 1H), 10.21 (s, 1H)

Example 23

1-Methylhomopiperazine (0.66 g, 5.77 mmol) was reacted according to the same procedure as Example 1 to give 4-(4-methylhomopiperazin-1-ylmethyl)-N-[2-fluoro-5-(4-(pyridin-3-yl)pyrimidin-2-yl)aminophenyl]benzamide (1.02 g).

$R_f$=0.2 (Chloroform:Methanol=1:1)

$^1$H-NMR (DMSO-$d_6$)=1.70-1.78 (m, 2H), 2.26 (s, 3H), 2.51-2.69 (m, 8H), 3.69 (s, 2H), 7.27-7.32 (m, 1H), 7.51-7.68 (m, 6H), 7.96-8.00 (m, 1H), 8.59-8.75 (m, 2H), 9.37 (s, 1H), 9.91 (s, 1H), 10.12 (s, 1H)

Example 24

Methanesulfonic acid (50 mg, 0.52 mmol) was reacted according to the same procedure as Example 2 to give 4-(4-methylhomopiperazin-1-ylmethyl)-N-[2-fluoro-5-(4-(pyridin-3-yl)pyrimidin-2-yl)aminophenyl]benzamide methanesulfonate (0.21 g).

$R_f$=0.5 (Methylene chloride:Ethyl acetate:Methanol: 25% Aqueous ammonia=60:10:30:1)

mp=125-127° C.

$^1$H-NMR (D$_2$O)=1.91 (m, 2H), 2.67 (s, 3H), 2.76 (s, 3H), 2.97 (m, 4H), 3.28 (m, 4H), 3.69 (s, 2H), 6.55-6.64 (m, 3H), 6.81-6.85 (m, 1H), 7.18-7.23 (d, 2H), 7.41-7.46 (d, 2H), 7.61 (m, 1H), 7.72-7.75 (m, 2H), 7.91 (m, 1H), 8.31 (s, 1H)

Example 25

1-Methylpiperazine (0.58 g, 5.77 mmol) and N-[4-fluoro-3-(4-chloromethylbenzoyl amino)-phenyl]-4-(3-pyridyl)-2-pyrimidine-amine (1 g, 2.31 mmol) were reacted according to the same procedure as Example 1 to give 4-(4-methylpiperazin-1-ylmethyl)-N-[2-fluoro-5-(4-(pyridin-3-yl)pyrimidin-2-yl)aminophenyl]benzamide (1.1 g).

$R_f$=0.2 (Chloroform:Methanol=1:1)

$^1$H-NMR (DMSO-$d_6$)=2.28 (s, 3H), 2.51 (s, 8H), 3.57 (s, 2H), 7.27-7.31 (m, 1H), 7.45-7.67 (m, 5H), 7.97-8.01 (d, 2H), 8.17 (m, 1H), 8.56-8.74 (m, 3H), 9.36 (s, 1H), 9.90 (s, 1H), 10.14 (s, 1H)

Example 26

Methanesulfonic acid (0.58 g, 6 mmol) was reacted according to the same procedure as Example 2 to give 4-(4-methylpiperazin-1-ylmethyl)-N-[2-fluoro-5-(4-pyridin-3-yl)pyrimidin-2-yl)aminophenyl]benzamide methanesulfonate (1.53 g).

$R_f$=0.5 (Methylene chloride:Ethyl acetate:Methanol: 25% Aqueous ammonia=60:10:30:1)

mp=174-176° C.

$^1$H-NMR (D$_2$O)=2.67 (s, 3H), 2.76 (s, 3H), 2.82 (m, 4H), 3.22 (m, 4H), 3.70 (s, 2H), 6.64-6.77 (m, 3H), 7.27-7.31 (m, 3H), 7.51 (d, 2H), 7.63 (d, 1H), 7.86 (d, 1H), 8.18 (d, 2H), 8.58 (s, 1H)

Example 27

1-Amino-4-methylpiperazine (0.66 g, 5.77 mol) and N-[4-fluoro-3-(4-chloromethyl benzoylamino)-phenyl]-4-(3-pyridyl)-2-pyrimidine-amine (1 g, 2.31 mmol) were reacted according to the same procedure as Example 3 to give 4-(4-methylpiperazin-1-ylaminomethyl)-N-[2-fluoro-5-(4-(pyridin-3-yl)pyrimidin-2-yl)aminophenyl]benzamide (0.63 g).

$R_f$=0.2 (Chloroform:Methanol=1:1)

$^1$H-NMR (DMSO-$d_6$)=2.15 (s, 3H), 2.37-2.41 (m, 8H), 3.55 (s, 2H), 7.27 (m, 1H), 7.45-7.67 (m, 6H), 7.95 (d, 2H), 8.21 (m, 1H), 8.55-8.74 (m, 3H), 9.36 (s, 1H), 9.90 (s, 1H), 10.12 (s, 1H)

Example 28

Methanesulfonic acid (0.18 g, 1.91 mmol) was reacted according to the same procedure as Example 4 to give 4-(4-methylpiperazin-1-ylaminomethyl)-N-[2-fluoro-5-(4-(pyridin-3-yl)pyrimidin-2-yl)aminophenyl]benzamide methanesulfonate (0.27 g).

$R_f$=0.5 (Methylene chloride:Ethyl acetate:Methanol: 25% Aqueous ammonia=60:10:30:1)

mp=142-144° C.

$^1$H-NMR (D$_2$O)=2.67 (s, 3H), 2.83 (s, 3H), 3.17-3.37 (m, 8H), 4.06 (s, 2H), 6.95-7.01 (m, 2H), 7.11 (d, 1H), 7.45 (d, 2H), 7.74-7.79 (m, 3H), 7.87-7.91 (m, 1H), 8.21 (d, 1H), 8.55 (d, 1H), 8.73 (d, 1H), 9.05 (s, 1H)

Example 29

1-Amino-4-methylpiperazine (1 g, 8.7 mmol) was reacted according to the same procedure as Example 3 to give 4-(4-methylpiperazin-1-ylaminomethyl)-N-[4-(4-(pyridin-3-yl) pyrimidin-2-yl)aminophenyl]benzamide (1.23 g).

$R_f$=0.4 (Chloroform:Methanol=1:1)

$^1$H-NMR (DMSO-$d_6$)=2.27 (s, 3H), 2.39-2.57 (m, 8H), 3.91 (s, 2H), 7.47-7.53 (m, 4H), 7.56-7.66 (m, 1H), 7.77-7.88 (m, 4H), 7.91-7.93 (m, 2H), 8.50-8.61 (m, 2H), 8.80 (d, 1H), 9.35 (s, 1H), 9.79 (s, 1H), 10.17 (s, 1H)

Example 30

Methanesulfonic acid (48 mg, 0.5 mmol) was reacted according to the same procedure as Example 4 to give 4-(4- methylpiperazin-1-ylaminomethyl)-N-[4-(4-(pyridin-3-yl) pyrimidin-2-yl)aminophenyl]benzamide methanesulfonate (0.17 g).

$R_f$=0.2 (Methylene chloride:Ethyl acetate:Methanol: 25% Aqueous ammonia=60:10:30:1)

mp=151-153° C.

$^1$H-NMR (D$_2$O)=2.71 (s, 3H), 2.81 (s, 3H), 3.21-3.23 (m, 4H), 3.31-3.41 (m, 4H), 3.99 (s, 2H), 6.91-6.94 (m, 1H), 7.11-7.31 (m, 7H), 7.60-7.63 (m, 2H), 8.13-8.17 (m, 2H), 8.43 (m, 1H), 8.73 (s, 1H)

Example 31

1-Methylpiperazine (1.2 ml, 10.38 mmol) was reacted according to the same procedure as Example 3 to give 4-(4-methylpiperazin-1-ylmethyl)-N-[4-fluoro-3-(4-(pyridin-3-yl)pyrimidin-2-yl)aminophenyl]benzamide (1.3 g).

$R_f$=0.2 (Chloroform:Methanol=1:1)

$^1$H-NMR (MeOD)=2.67 (m, 8H), 3.03 (s, 3H), 3.69 (s, 2H), 7.16-7.21 (m, 2H), 7.43-7.59 (m, 4H), 7.93-7.97 (d, 2H), 8.53-8.56 (d, 1H), 8.63-8.69 (m, 3H), 9.31 (s, 1H)

Example 32

Methanesulfonic acid (186 μl, 2.87 mmol) was reacted according to the same procedure as Example 4 to give 4-(4-methylpiperazin-1-ylmethyl)-N-[4-fluoro-3-(4-(pyridin-3-yl)pyrimidin-2-yl)aminophenyl]benzamide methanesulfonate (790 mg).

$R_f$=0.21 (Methylene chloride:Ethyl acetate:Methanol: 25% Aqueous ammonia 60:10:30:1)

mp=172-174° C.

$^1$H-NMR (D$_2$O)=2.70 (s, 3H), 2.87 (s, 3H), 3.12 (m, 4H), 3.38 (m, 4H), 3.96 (s, 2H), 6.46 (br, 1H), 6.58-6.69 (m, 1H), 6.83-6.86 (d, 1H), 7.29-7.43 (m, 5H), 7.88-7.90 (d, 1H), 8.10-8.13 (m, 1H), 8.23-8.25 (d, 1H), 8.40-8.44 (d, 1H), 8.72 (s, 1H)

Example 33

1-Methylhomopiperazine (1.3 ml, 10.38 mmol) was reacted according to the same procedure as Example 1 to give 4-(4-methylhomopiperazin-1-ylmethyl)-N-[4-fluoro-3-(4-(pyridin-3-yl)pyrimidin-2-yl)aminophenyl]benzamide (580 mg).

$R_f$=0.1 (Chloroform:Methanol=1:1)

$^1$H-NMR (MeOD)=1.96-2.00 (m, 2H), 2.70 (s, 3H), 2.76-2.87 (m, 4H), 3.06-3.19 (m, 4H), 3.78 (s, 2H), 7.18 (m, 1H), 7.43-7.46 (m, 1H), 7.52-7.59 (m, 4H), 7.92-7.96 (d, 2H), 8.54-8.56 (d, 1H), 8.63-8.70 (m, 3H), 9.32 (s, 1H)

Example 34

Methanesulfonic acid (75.3 μl, 1.16 mmol) was reacted according to the same procedure as Example 2 to give 4-(4-methylhomopiperazin-1-ylmethyl)-N-[4-fluoro-3-(4-(pyridin-3-yl)pyrimidin-2-yl)aminophenyl]benzamide methanesulfonate (790 mg).

$R_f$=0.13 (Methylene chloride:Ethyl acetate:Methanol: 25% Aqueous ammonia=60:10:30:1)

mp=158-160° C.

$^1$H-NMR (D$_2$O)=2.18 (br, 2H), 2.67 (s, 3H), 2.88 (s, 3H), 3.38-3.45 (m, 4H), 3.65-3.71 (m, 4H), 4.34 (s, 2H), 6.56 (m, 1H), 6.74-6.84 (m, 1H), 6.89-6.92 (d, 1H), 7.21-7.28 (m, 1H), 7.42-7.46 (d, 2H), 7.56-7.60 (d, 2H), 7.67-8.00 (d, 1H), 8.18-8.30 (m, 3H), 8.71 (s, 1H)

Example 35

Piperidine (1.5 g, 17.6 mmol) was reacted according to the same procedure as Example 1 to give 4-(piperidin-1-ylmethyl)-N-[3-(4-(pyridin-3-yl)pyrimidin-2-yl)aminophenyl] benzamide (2.2 g).

$R_f$=0.43 (Chloroform:Methanol=1:1)

$^1$H-NMR (DMSO-d$_6$)=2.17 (s, 3H), 2.53-2.81 (m, 10H), 3.71 (s, 2H), 7.33 (s, 2H), 7.51-7.63 (m, 6H), 7.95-7.99 (d, 2H), 8.47 (s, 1H), 8.49-8.77 (m, 2H), 9.43 (s, 1H), 9.89 (s, 1H), 10.19 (s, 1H)

Example 36

Methanesulfonic acid (0.248 g, 2.5 mmol) was reacted according to the same procedure as Example 2 to give 4-(piperidin-1-ylmethyl)-N-[3-(4-(pyridin-3-yl)pyrimidin-2-yl) aminophenyl]benzamide methanesulfonate (0.83 g).

$R_f$=0.2 (Methylene chloride:Methanol: 25% Aqueous ammonia=150:10:1)

mp=173-175° C.

$^1$H-NMR (D$_2$O)=2.63 (s, 3H), 2.81 (s, 3H), 3.41-3.53 (m, 4H), 3.61-3.69 (m, 6H), 4.31 (s, 2H), 7.11-7.15 (m, 1H), 7.21-7.31 (m, 3H), 7.53-7.57 (m, 2H), 7.81-7.95 (m, 4H), 8.33-8.37 (m, 1H), 8.55 (s, 1H), 9.07 (s, 1H), 9.22 (s, 1H)

Example 37

Acetic acid (0.58 g, 9.2 mmol) was reacted according to the same procedure as Example 2 to give 4-(4-methylhomopiperazin-1-ylmethyl)-N-[4-(4-(pyridin-3-yl)pyrimidin-2-yl) aminophenyl]benzamide acetate (1.53 g).

$R_f$=0.2 (Methylene chloride:Methanol: 25% Aqueous ammonia=150:10:1)

mp=197-199

$^1$H-NMR (D$_2$O)=1.68 (m, 2H), 2.53 (s, 3H), 2.67 (s, 3H), 3.01-3.06 (m, 2H), 3.33-3.47 (m, 6H), 3.99 (s, 2H), 6.95-6.99 (m, 1H), 7.16-7.37 (m, 7H), 7.61-7.65 (m, 2H), 8.11-8.15 (m, 2H), 8.41 (m, 1H), 8.69 (s, 1H)

Example 38

Acetic acid (0.24 g, 3.8 mmol) was reacted according to the same procedure as Example 2 to give 4-(4-methylhomopiperazin-1-ylmethyl)-N-[4-methyl-3-(4-(pyridin-3-yl)pyrimidin-2-yl)aminophenyl]benzamide acetate (0.61 g).

$R_f$=0.2 (Methylene chloride:Methanol: 25% Aqueous ammonia=150:10:1)

mp=165-167° C.

$^1$H-NMR (D$_2$O)=2.07 (s, 2H), 2.58 (s, 3H), 2.61 (s, 3H), 2.77 (s, 3H), 3.41 (m, 4H), 3.63 (m, 4H), 4.41 (s, 2H), 7.01 (d, 1H), 7.17 (s, 3H), 7.38-7.41 (d, 2H), 7.63-7.75 (m, 3H), 8.20 (d, 1H), 8.47 (d, 1H), 8.61 (d, 1H), 8.93 (s, 1H)

Example 39

Acetic acid (0.18 g, 2.8 mmol) was reacted according to the same procedure as Example 4 to give 4-(4-methylpiperazin-1-ylaminomethyl)-N-[4-methyl-3-(4-(pyridin-3-yl)pyrimidin-2-yl)aminophenyl]benzamide acetate (0.31 g).

$R_f$=0.2 (Methylene chloride:Methanol: 25% Aqueous ammonia=150:10:1)

mp=153-155° C.

$^1$H-NMR (D$_2$O)=1.37 (s, 3H), 2.53 (s, 3H), 2.67 (s, 3H), 2.83-2.88 (m, 4H), 2.97-3.11 (m, 4H), 3.43 (s, 2H), 6.79 (d,

1H), 6.99-7.27 (m, 6H), 7.41 (d, 2H), 7.99 (m, 1H), 8.02 (d, 1H), 8.22-8.27 (m, 1H), 8.57 (s, 1H)

Example 40

Acetic acid (0.3 g, 4.7 mmol) was reacted according to the same procedure as Example 4 to give 4-(4-methylpiperazin-1-ylaminomethyl)-N-[4-(4-(pyridin-3-yl) pyrimidin-2-yl) aminophenyl]benzamide acetate (0.57 g).

$R_f$=0.2 (Methylene chloride:Methanol: 25% Aqueous ammonia=150:10:1)

mp=169-171° C.

$^1$H-NMR ($D_2O$)=2.65 (s, 3H), 2.78 (s, 3H), 3.20-3.25 (m, 4H), 3.30-3.43 (m, 4H), 4.00 (s, 2H), 6.87-6.95 (m, 1H), 7.11-7.38 (m, 7H), 7.61-7.65 (m, 2H), 8.15-8.19 (m, 2H), 8.43 (m, 1H), 8.81 (s, 1H)

Example 41

Hydrochloric acid (2.2 g, 60.2 mmol) was reacted according to the same procedure as Example 2 to give 4-(4-methyl-homopiperazin-1-ylmethyl)-N-[4-(4-(pyridin-3-yl)pyrimidin-2-yl)aminophenyl]benzamide hydrochloride (0.83 g).

$R_f$=0.2 (Methylene chloride:Methanol: 25% Aqueous ammonia=150:10:1)

mp=197-199° C.

$^1$H-NMR ($D_2O$)=1.77 (m, 2H), 2.43 (s, 3H), 3.00-3.07 (m, 2H), 3.31-3.43 (m, 6H), 4.01 (s, 2H), 7.03-7.15 (m, 1H), 7.19-7.33 (m, 7H), 7.71-7.83 (m, 2H), 8.15-8.18 (m, 2H), 8.41 (m, 1H), 8.71 (s, 1H)

Example 42

Hydrochloric acid (1.3 g, 35.6 mmol) was reacted according to the same procedure as Example 4 to give 4-(4-methylpiperazin-1-ylaminomethyl)-N-[4-methyl-3-(4-(pyridin-3-yl)pyrimidin-2-yl)aminophenyl]benzamide hydrochloride (0.21 g).

$R_f$=0.2 (Methylene chloride:Methanol: 25% Aqueous ammonia=150:10:1)

mp=173-175° C.

$^1$H-NMR ($D_2O$)=1.77 (s, 3H), 2.55 (s, 3H), 2.85-2.93 (m, 4H), 2.97-3.11 (m, 4H), 3.51 (s, 2H), 6.81 (d, 1H), 7.00-7.25 (m, 6H), 7.43 (d, 2H), 8.00 (m, 1H), 8.05 (d, 1H), 8.25-8.33 (m, 1H), 8.63 (s, 1H)

Example 43

Hydrochloric acid (2.5 g, 68.4 mmol) was reacted according to the same procedure as Example 4 to give 4-(4-methylpiperazin-1-ylaminomethyl)-N-[4-(4-(pyridin-3-yl)pyrimidin-2-yl)aminophenyl]benzamide hydrochloride (0.43 g).

$R_f$=0.2 (Methylene chloride:Methanol: 25% Aqueous ammonia=150:10:1)

mp=183-185° C.

$^1$H-NMR ($D_2O$)=2.67 (s, 3H), 3.21-3.30 (m, 4H), 3.33-3.47 (m, 4H), 4.07 (s, 2H), 6.85-6.95 (m, 1H), 7.13-7.47 (m, 7H), 7.63-7.68 (m, 2H), 8.17-8.21 (m, 2H), 8.47 (m, 1H), 8.88 (s, 1H)

Experiment 1

In the present experiment, the inhibitory activity of the compound of formula (1) was determined against the growth of K562 cancer cell. First, the cells were allowed to stand in RPMI (Roswell Park Memorial Institute)—1640 medium containing 10% (v/v) fetal bovine serum in an incubator of 37° C. and 5% by volume of $CO_2$. The cancer cells (1000 cells) were transferred to a 96-well plate, and the test compound was diluted. The plate was allowed to stand under the above mentioned conditions for 2 days. After this treatment, to the cells was added 0.2% MTT (3-[4,5-dimethylthiazol-2-yl]-2,5-diphenyltetrazolium bromide) solution, and the resulting mixture was allowed to stand under the constant temperature-condition for 4 hours. The supernatant was removed to leave the resulting crystal. DMSO was added to dissolve the crystal, and the absorbance of the solution was measured at 540 nm. $IC_{50}$ value was calculated using a computer system according to the following formula:

$$(OD_{540}(test)-OD_{540}(initial)/OD_{540}(control)-OD_{540}(initial))\times 100$$

In the above formula, the $IC_{50}$ value is defined as the concentration of the active compound when the number of cells per well at the end of constant temperature-treatment is 50% of the number of cells in the control medium.

The $IC_{50}$ values [μg/ml] in the following Table 1 were obtained for the example compounds according to the present invention.

TABLE 1

| Example No. | $IC_{50}$ [μg/ml] |
|---|---|
| Imatinib mesylate | 0.54 |
| 2 | 1.20 |
| 4 | <0.10 |
| 6 | 20.51 |
| 8 | 27.58 |
| 10 | 3.85 |
| 12 | 10.21 |
| 14 | 8.95 |
| 16 | >50.0 |
| 20 | 34.7 |
| 22 | 10.0 |
| 24 | 19.05 |
| 28 | 8.63 |
| 30 | 22.81 |
| 32 | 8.06 |
| 34 | 7.17 |
| 36 | 11.32 |
| 41 | 5.61 |
| 42 | 0.30 |
| 43 | >50.0 |

As can be seen in the above Table 1, the existing drug of Imatinib mesylate showed an $IC_{50}$ value of 0.54 μg/ml against the CML cell line, K562, whereas the compound of Example 4 of the present invention showed an $IC_{50}$ value of 0.1 μg/ml or less, which corresponds to 5 times improved activity. Further, the compound of Example 42 showed much higher activity than Imatinib mesylate.

Experiment 2

In the present experiment, the inhibitory activity of the compound of formula (1) was determined against the growth of L1210 cancer cell. The test was performed according to the same procedure as Experiment 1. Thus obtained $IC_{50}$ values [μg/ml] are represented in the following Table 2.

TABLE 2

| Example No. | $IC_{50}$ [μg/ml] |
|---|---|
| Imatinib mesylate | 32.90 |
| 2 | 7.60 |
| 4 | 26.90 |

TABLE 2-continued

| Example No. | IC$_{50}$ [μg/ml] |
|---|---|
| 6 | 3.24 |
| 8 | 7.38 |
| 10 | 3.40 |
| 12 | 0.99 |
| 20 | 4.32 |
| 22 | 4.46 |
| 36 | 5.95 |

As can be seen in the above Table 2, the existing drug of Imatinib mesylate showed an IC$_{50}$ value of 32.90 μg/ml against the leukemia cell line, L1210, whereas the compounds of Examples 12 and 6 of the present invention showed IC$_{50}$ values of 0.99 μg/ml and 3.24 μg/ml, respectively, which corresponds to 32 times and 10 times improved activity, respectively. Further, all the other example compounds showed much higher activity than Imatinib mesylate.

Experiment 3

In the present experiment, the inhibitory activity of the compound of formula (1) was determined against the growth of U937 cancer cell. The test was performed according to the same procedure as Experiment 1. Thus obtained IC$_{50}$ values [μg/ml] are represented in the following Table 3.

TABLE 3

| Example No. | IC$_{50}$ [μg/ml] |
|---|---|
| Imatinib mesylate | 28.75 |
| 2 | 0.70 |
| 4 | 0.90 |
| 6 | 5.14 |
| 8 | 9.44 |
| 10 | 7.30 |
| 12 | 3.41 |
| 20 | 9.51 |
| 22 | 8.61 |
| 36 | 6.91 |

As can be seen in the above Table 3, the existing drug of Imatinib mesylate showed an IC$_{50}$ value of 28.75 μg/ml against the monocyte like leukemia cell line, U937, whereas the compounds of Examples 2 and 4 of the present invention showed IC$_{50}$ values of 0.7 μg/ml and 0.9 μg/ml, respectively, which corresponds to 40 times and 30 times improved activity, respectively. Further, all the other example compounds showed much higher activity than Imatinib mesylate.

Experiment 4

In the present experiment, the inhibitory activities of Imatinib mesylate and the compounds of Examples 2, 4, and 10 were determined against the growth of several cancer cells. The test was performed according to the same procedure as Experiment 1. Thus obtained IC$_{50}$ values [μg/ml] are represented in the following Table 4.

TABLE 4

| Cancer Cell | Imatinib mesylate | Example 2 | Example 4 | Example 10 |
|---|---|---|---|---|
| A549 | 37.18 | 27.6 | 46.6 | 3.50 |
| KATO III | 32.58 | 30.04 | 32.35 | 3.26 |
| KB | 47.54 | 31.59 | 35.04 | 8.99 |
| HL-60 | 35.68 | 17.74 | 27.79 | 4.28 |
| SK-OV-03 | >50.0 | 37.99 | >50.0 | 25.50 |
| MCF-7 | >50.0 | 36.22 | >50.0 | 6.96 |
| DU-145 | 9.04 | 30.33 | 41.26 | 5.51 |
| KG-1 | 31.22 | 7.31 | >50.0 | 3.31 |
| RPMI-6666 | 33.76 | 14.72 | 33.80 | 2.12 |
| SNU-182 | 44.00 | 24.72 | 48.04 | 7.94 |

As can be seen in the above Table 4, the compound of Example 2 according to the present invention showed IC$_{50}$ values of ¼ time and ½ time or less, than Imatinib mesylate against KG-1 and RPMI-6666, respectively. Further, the compound of Example 10 showed improved activity than Imatinib mesylate against all of lung cancer cell (A549), gastric cancer cell (KATO III), oral epithelial cancer cell (KB), hematologic malignancy cell (HL-60), ovarian cancer cell (SK-OV-03), breast cancer cell (MCF-7), prostatic cancer cell (DU-145), acute myelogenous leukemia cell (KG-1), lymphoma cell (RPMI-6666), and hepatoma cell (SNU-182) as demonstrated by its IC$_{50}$ values of 1/10, 1/10, ⅕, ⅛, ½, 1/7, ½, 1/10, 1/15, and ⅕ time or less, than Imatinib mesylate, respectively.

Summarizing Tables 1 to 4, the compound of Example 4 showed activity of 5 times or more against the CML cell line, K562, than the standard drug of Imatinib mesylate, and also showed a similarly excellent effect against the other cell lines, and so it is expected to be a candidate that is a similar type, but has a far superior effect, to Imatinib mesylate. The compound of Example 42 is also expected to have a better effect than Imatinib mesylate. Most example compounds according to the present invention represented superior activity against U937 and L1210 to Imatinib mesylate, and particularly, the compounds of Examples 2 and 4 showed a far superior effect against U937, and the compounds of Examples 12 and 6 against L1210. Therefore, it is anticipated that a new therapeutic agent may be developed against these cancers.

On the other hand, the compounds of Examples 2 and 10 exhibited far superior activity to Imatinib mesylate against the other cancer cells except K562. Particularly, the compound of Example 2 showed high activity against acute myelogenous leukemia cell of KG-1, and the compound of Example 10 against lymphoma cell of RPMI-6666, lung cancer cell of A549, gastric cancer cell of KATO III, hematologic malignancy cell of HL-60, breast cancer cell of MCF-7, prostatic cancer cell of DU-145, acute myelogenous leukemia cell of KG-1, hepatoma cell of SNU-182, etc., and so these compounds are expected to be developed as new therapeutic agents against the other cancers besides the CML.

Experiment 5

In the present experiment, the inhibitory activities of Imatinib mesylate, cisplatin, 5-Fu, and the compounds of Examples 4 and 10 were determined against the growth of colon cancer cell, pancreatic cancer cell, encephalophyma cell, rectal cancer cell, cervical cancer cell, and bladder cancer cell. The test was performed according to the same procedure as Experiment 1. Thus obtained IC$_{50}$ values [μg/ml] are represented in the following Table 5.

TABLE 5

|  | Cisplatin | 5-FU | Imatinib mesylate | Example 4 | Example 10 |
|---|---|---|---|---|---|
| PANC-1 | 41.55 | 553.8 | 53.05 | 53.77 | 4.62 |
| CAPAN-2 | 496.9 | 1000> | 58.57 | 56.27 | 45.86 |
| SNU-C1 | 302 | 95.3 | 30 | 10 | 1.2 |
| CMT-93 | 0.67 | 1.1 | 7.27 | 8.39 | 4.04 |
| HeLa 229 | 0.9 | 81.03 | 46.9 | 48.5 | 5.5 |
| A172 | 5.7 | 99 | 44.5 | 39.3 | 5.5 |
| HT-1197 | 7.5 | 98.5 | 55 | 50.1 | 1.7 |

As can be seen in the above Table 5, the compound of Example 10 according to the present invention showed improved activity against colon cancer cell of SNU-C1 and pancreatic cancer cell of PANC-1, by more than 25 and 10 times, respectively, than Imatinib mesylate, but similar activity against another pancreatic cancer cell of CAPAN-2. The compound of Example 10 also showed improved activity against encephalophyma cell of A172, rectal cancer cell of CMT-93, cervical cancer cell of HeLa229, and bladder cancer cell of HT-1197, by more than 8, 1.5, 8, and 32 times, respectively, than Imatinib mesylate. In the comparison experiment with cisplatin and 5-Fu, the compound of Example 10 showed improved activity against SNU-C1 by more than 250 and 80 times, against PANC-1 by more than 9 and 120 times, and against CAPAN-2 by more than 10 and 20 times, respectively. Further, it showed similar activity to cisplatin, or improved activity compared with 5-Fu by more than 18 times, against A172, respectively. It also showed improved activity against HT-1197 by more than 4.4 and 55 times compared with cisplatin and 5-Fu, respectively.

On the other hand, the compound of Example 4 showed 3 times more improved activity than Imatinib mesylate against SNU-C1, or similarly improved activity to the same against pancreatic cancer, encephalophyma, rectal cancer, cervical cancer, and bladder cancer cells. In the comparison experiment with cisplatin and 5-Fu, the compound of Example 4 showed 30 and 9 times more improved activity against SNU-C1, respectively. Further, it showed a similar activity to cisplatin or 10 times more improved activity than 5-Fu against PANC-1, and 9 and 17 times more improved activity than cisplatin and 5-Fu against CAPAN-2, respectively.

Therefore, the compounds of Examples 4 and 10 are expected to be new and potent therapeutic agents for the treatment of pancreatic cancer, colon cancer, encephalophyma, bladder cancer, rectal cancer, cervical cancer, etc. besides the CML.

Experiment 6

Comparative Pharmacokinetic Test in White Rats

On the previous day to the test, white rats (Sprague-Dawley, 250~280 g, male) were put under anesthesia by pentobarbital sodium (50 mg/kg, I.P.). Then, cannula (polyethylene tube; diameter: 0.58 mm) was introduced into the rats via the carotid artery and jugular vein, and drawn out to the back. After the operation, the rats were fasted for 16 hours and used for the test. Imatinib mesylate (100 mg/kg) and the compounds of Example 2 (20 mg/kg) and 4 (50 mg/kg) were orally administered, and the compound of Example 10 (50 mg/kg) was intravenously administered. Blood was collected in 0, 0.5, 1, 1.5, 2, 2.5, 3, 3.5, 4, 4.5, 5, 6, 8, 10, 12, and 24 hours from the carotid artery. The samples for HPLC analysis were prepared using the collected blood according to the following procedure and were analyzed under the following conditions.

Preparation of the Samples for HPLC Analysis

Blood was collected by an amount of 0.5 ml at each prearranged time and centrifuged at 15000 rpm for 7 minutes to separate 200 μl of plasma. In order to remove proteins, MeOH was added in an amount of 400 μl, twice as much as the amount of plasma, and the mixture was shaken for 30 minutes. The mixture was centrifuged again at 15000 rpm for 5 minutes to give protein free supernatant, which was then analyzed by HPLC.

HPLC Analysis Conditions

Flow rate: 1.0 μl/min, UV detection at 267 nm

Column: 4.6×150 mm, 5C18-AR-II, COSMOSIL

Eluent: Mixture of ion pair sample (420 ml) and MeOH (580 ml)

Ion pair sample: 7.5 g of 1-octanesulfonic acid was dissolved in 800 ml of water. The resulting mixture was adjusted to pH 2.5 using phosphoric acid and diluted with water to 1000 ml volume.

When Imatinib mesylate and the compound of Example 4 were administered per oral to the white rats in a dosage of 100 mg/kg, it was confirmed by the HPLC analysis that Cmax (maximum blood concentration) and AUC (area under the curve of time-blood concentration) of the compound of Example 4 were about twice as much as those of Imatinib mesylate. Accordingly, pharmacokinetic test was carried out by orally administering the compound of Example 4 in a dosage of 50 mg/kg, half of the above dosage, carrying out the test according to the same procedure as above, and comparing the result with that of Imatinib mesylate which was administered orally in a dosage of 100 mg/kg. Here, the pharmacokinetic parameters are Tmax (time to reach the maximum blood concentration), Cmax (maximum blood concentration), AUC (area under the curve of time-blood concentration), and $T_{1/2}$ (half time in blood), and the AUC was calculated under trapezoid rule (see Tables 6, 7 and FIGS. 1, 2).

TABLE 6

|  | Imatinib mesylate (100 mg/kg, P.O.) | Example 2 (50 mg/kg, P.O.) | Example 4 (50 mg/kg, P.O.) |
|---|---|---|---|
| Tmax (hr) | 2.3 | 1.5 | 2 |
| Cmax (μg/ml) | 2.724 | 2.197 | 3.155 |
| AUC | 26.461 | 26.181 | 22.951 |

TABLE 7

|  | Example 10 (50 mg/kg, I.V.) |
|---|---|
| $T_{1/2}$ (hr) | 1.37 |
| AUC | 8.92 |

Figure 1:
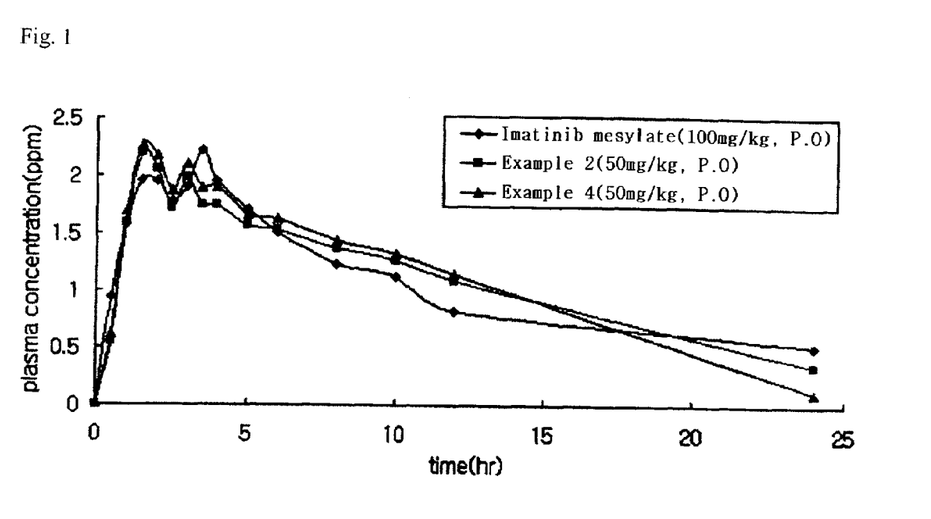
FIG. 1 shows the pharmacokinetic data of the compounds of Examples 2 and 4 according to the present invention compared with a standard drug of Imatinib mesylate.
Figure 2:
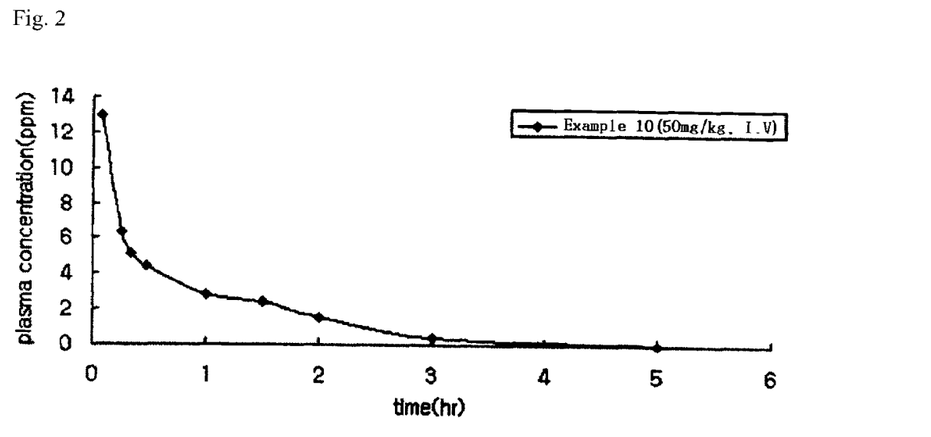
FIG. 2 shows the pharmacokinetic data of the compound of Example 10 when it is administered via intravenous injection.

As shown in the above Tables 6 and 7, although the concentration of administration of Examples 2 and 4 is half of that of Imatinib mesylate, it was identified that their pharmacokinetic parameters of Tmax, Cmax, and AUC are similar to those of Imatinib mesylate with no statistical significance (Table 6 and FIG. 1). Further, the compound of Example 10 showed $T_{1/2}$ of 1.37 and AUC of 8.92 when it is intravenously administered (Table 7, FIG. 2). On the basis of these results, it may be concluded that the compounds of Examples 2 and 4 exhibit the same effect as Imatinib mesylate when they are clinically applied at about half lower daily dosage than that of Imatinib mesylate. Therefore, the compound of the present invention has a superior therapeutic effect and various advantages in cost, etc., and also can be formulated into an oral dosage form (tablet or capsule) or an injection form when industrially manufactured.

Experiment 7

Acute Toxicity Test in Mice (Oral Administration)

In order to determine the acute toxicity of the compound of the present invention when the compound is orally administered, mice (ICR, 24~26 g) were fasted for 16 hours. One group consists of 10 males and 10 females. The first group is the control group and physiological saline was administered per oral to this group. The compounds of Examples 2 and 4 were orally administered in a dosage of 2000 mg/kg, the maximum dosage in acute toxicity test, to each test group. After the administration, clinical conditions of the mice were observed for 14 days and weight change was also measured. On the last day of the test, $14^{th}$ day from the start, the mice were subjected to an autopsy in order to examine changes of the internal organs. During the period of observation, neither abnormal response nor specific autopsy result was observed. Also, the body weights of the test groups do not show any change with statistical significance when compared with the control group. Further, since no mouse died during the test period, it was confirmed that the compounds of Examples 2 and 4 have $LD_{50}$ of 2,000 mg/kg or more. This means that the compounds of the present invention including those of Examples 2 and 4 are safe in the aspect of acute toxicity.

Acute Toxicity Test in Mice (Intravenous Administration)

In this test, the acute toxicity of the compound of the present invention when the compound is intravenously administered was determined on mice (ICR, 24~26 g). One group consists of 10 males and 10 females. The first group is the control group and physiological saline was intravenously administered to this group. The compound of Example 10 was intravenously administered in dosages of 25, 50, 75, and 100 mg/kg, respectively, to each test group. After the administration, clinical conditions of the mice were observed for 14 days and weight change was also measured. On the last day of the test, $14^{th}$ day from the start, the mice were subjected to an autopsy in order to examine changes of the internal organs. During the period of observation, the control group and the test group of 25 mg/kg dosage showed neither abnormal response nor specific autopsy. However, the test groups of 50 and 75 mg/kg dosage showed weak trembling immediately after the administration, but were quickly recovered within 1 hour. No mouse died in these test groups. Further, in the test group of 100 mg/kg dosage, 8 mice among 10 died within 10 minutes after the administration. The recovered mice, however, showed neither abnormal response nor specific autopsy. Based on this experiment, it was confirmed that the compound of Example 10 has $LD_{50}$ of 75~100 mg/kg when intravenously administered. Considering that cisplatin shows $LD_{50}$ of 11 mg/kg when it is intravenously administered to a mouse, the above result means that the compounds of the present invention are much safer than cisplatin.

Experiment 8

Anti-Cancer Activity in Sarcoma Animal Model

The anti-cancer activity against sarcoma-180 was determined using ICR mouse (22~25 g, male). Sarcoma-180 (0.1 ml; $5 \times 10^7$ cells/ml) was hypodermically implanted to the left inguinal area of the mouse. After 72 hours from the hypodermic implantation, physiological saline was intravenously administered to the control group. For the test groups, the compound of Example 10 dissolved in physiological saline in a concentration of 25 or 50 mg/kg was intravenously administered three times at intervals of 4 days. On the $30^{th}$ day from the implantation of the tumor cell, the mice were sacrificed to take out the induced solid tumors. The solid tumors were weighed, the average weight of the tumors was obtained, and the percent inhibition ratio was calculated according to the following formula:

Inhibition ratio (I.R.)(%)=$[(Cw-Tw)/Cw] \times 100$ in the above formula

I.R. represents the percent inhibition ratio,

Cw represents the average weight of tumor of the control group; and

Tw represents the average weight of tumor of the test group.

The test for anti-cancer activity using sarcoma-180, as can be seen from the following Table 8, shows that the test groups of 25 and 50 mg/kg dosage have the percent inhibition ratios of 36.1 and 63.0%, respectively, compared to the control group. Therefore, it was confirmed that the percent inhibition ratio is dependent on the concentration of the compound used, and also the compound of the present invention has an excellent therapeutic effect against sarcoma.

Table 8
Anti-Cancer Activity of the Compound of Example 10 on a Mouse Implanted with Sarcoma 180

|  | Average tumor weight (Mean ± S.E.) | Percent Inhibition Ratio (I.R.) |
|---|---|---|
| Control group | 3.27 ± 1.2 | — |
| Test group (25 mg/kg) | 2.09 ±1.4 | 36.1% |
| Test group (50 mg/kg) | 1:21 ± 1.2 | 63.0% |

The invention claimed is:

1. N-phenyl-2-pyrimidine-amine derivative represented by the following formula (1):

(1)

and its salt, in which $R_1$ represents 3-pyridyl or 4-pyridyl, $R_2$ and $R_3$ each represent hydrogen or lower alkyl, $R_6$ or $R_7$ represents a radical having the following formula (2):

(2)

wherein X represents oxygen or NH, n=0 or 1, and $R_9$ represents 4-methylhomopiperazine when n=0, or 4-methylpiperazine when n=1, and $R_4$, $R_5$, $R_7$, and $R_8$ each represent hydrogen, or one or two thereof each represent halogen, lower alkyl, or lower alkoxy when $R_6$ represents the radical of the above formula (2), or $R_4$ represents hydrogen and one or two of $R_5$, $R_6$, and $R_8$ each represent halogen, lower alkyl or lower alkoxy, or $R_4$ represents methyl or methoxy, $R_5$, $R_6$, and $R_8$ represent hydrogen, and $R_9$ represents 4-methylhomopiperazine, when $R_7$ represents the radical of the above formula (2);

with the proviso that the derivative is not a compound wherein $R_4$ represents hydrogen and two of $R_5$, $R_6$, and $R_8$ represent halogen, lower alkyl or lower alkoxy; and the derivative is not a compound wherein $R_4$ represents hydrogen and one or two of $R_5$, $R_6$, and $R_8$ represent alkoxy.

2. The compound of claim 1 wherein
$R_1$ represents 3-pyridyl,
$R_2$ and $R_3$ each represent hydrogen,
$R_6$ or $R_7$ represents a radical having the following formula (2):

(2)

wherein X represents oxygen or NH, n=0 or 1, and $R_9$ represents 4-methylhomopiperazine when n=0, or 4-methylpiperazine when n=1, and $R_4$, $R_5$, $R_7$, and $R_8$ each represent hydrogen, or one or two thereof each represent fluoro, methyl, or methoxy when $R_6$ represents the radical of the above formula (2), or $R_4$ represents hydrogen and one or two of $R_5$, $R_6$, and $R_8$ each represent fluoro, methyl, or methoxy, or $R_4$ represents methyl or methoxy, $R_5$, $R_6$, and $R_8$ represent hydrogen, when $R_7$ represents the radical of the above formula (2);

with the proviso that the derivative is not a compound wherein $R_4$ represents hydrogen and two of $R_5$, $R_6$, and $R_8$ represent fluoro, methyl or methoxy; and the derivative is not a compound wherein $R_4$ represents hydrogen and one or two of $R_5$, $R_6$, and $R_8$ represent methoxy.

3. The compound of claim 1 wherein $R_1$ represents 3-pyridyl, $R_2$, $R_3$, $R_4$, $R_5$, $R_7$, and $R_8$ each represent hydrogen, and $R_6$ represents the radical of formula (2) wherein n=0 and $R_9$ represents 4-methylhomopiperazine, or n=1, X represents NH, and $R_9$ represents 4-methylpiperazine.

4. The compound of claim 1 wherein $R_1$ represents 3-pyridyl, $R_2$ and $R_3$ each represent hydrogen, $R_4$ represents methyl, $R_5$, $R_6$ and $R_8$ each represent hydrogen, and $R_7$ represents the radical of formula (2) wherein n=1, X represents NH, and $R_9$ represents 4-methylpiperazine.

5. A pharmaceutical composition comprising an effective amount of the compound of formula (1) or its salt as defined in claim 1 as an active ingredient together with pharmaceutically acceptable inert carriers.

6. The composition of claim 5 which is used as an oral preparation.

7. The composition of claim 5 which is used as an injection.

* * * * *